(12) United States Patent
Yoshida et al.

(10) Patent No.: US 11,980,517 B2
(45) Date of Patent: May 14, 2024

(54) ELECTRIC TOOTHBRUSH AND METHOD FOR OPERATING AN ELECTRIC TOOTHBRUSH

(71) Applicants: Colgate-Palmolive Company, New York, NY (US); OMRON HEALTHCARE CO., LTD, Kyoto (JP)

(72) Inventors: Hideaki Yoshida, Kyoto (JP); Mamoru Katano, Kyoto (JP); Masashi Kitamura, Kyoto (JP); Sakae Morikawa, Kyoto (JP)

(73) Assignees: Colgate-Palmolive Company, New York, NY (US); Omron Healthcare Co., Ltd., Kyoto (JP)

( * ) Notice: Subject to any disclaimer, the term of this patent is extended or adjusted under 35 U.S.C. 154(b) by 693 days.

(21) Appl. No.: 16/949,926

(22) Filed: Nov. 20, 2020

(65) Prior Publication Data

US 2021/0068934 A1    Mar. 11, 2021

Related U.S. Application Data

(62) Division of application No. 15/735,367, filed as application No. PCT/US2016/036628 on Jun. 9, 2016, now Pat. No. 10,869,741.

(30) Foreign Application Priority Data

Jun. 12, 2015 (JP) .................. 2015-119561
Jun. 12, 2015 (JP) .................. 2015-119562
Jun. 18, 2015 (JP) .................. 2015-122897

(51) Int. Cl.
*A61C 17/22* (2006.01)
*A61B 5/00* (2006.01)
(Continued)

(52) U.S. Cl.
CPC .......... *A61C 17/221* (2013.01); *A61B 5/0088* (2013.01); *A61C 17/22* (2013.01);
(Continued)

(58) Field of Classification Search
CPC ... A61C 17/221; A61C 17/3481; A61C 17/02; A61C 17/0202; A61C 17/3472; A61C 17/3409; A61C 17/3463; A61C 17/3454
See application file for complete search history.

(56) References Cited

U.S. PATENT DOCUMENTS 5,301,381 A    4/1994 Klupt
6,725,490 B2   4/2004 Blaustein et al.
(Continued)

FOREIGN PATENT DOCUMENTS

CA    2895445    6/2014
CN    1395477    2/2003
(Continued)

OTHER PUBLICATIONS

International Search Report and the Written Opinion of the International Searching Authority issued in International Application PCT/US2016/036628 dated Jan. 31, 2017.

*Primary Examiner* — Laura C Guidotti

(57) ABSTRACT

An electric toothbrush that detects plaque on the teeth, ensures accurate plaque detection, and performs cleaning of plaque. The electric toothbrush may include a body having a gripping part and a stem with a brush unit detachably coupled to the body. The electric toothbrush may include a light emitting element for emitting light onto the tooth and a light receiving element for receiving light that reflects off of the tooth. A controller may be included to determine an amount of plaque on the tooth based on the amount of reflected light detected. The electric toothbrush may also include a fluid dispensing system that dispenses fluid based on the amount of reflected light detected. In some aspects, (Continued)

the electric toothbrush may operate in multiple oscillation modes, and it may only dispense fluid in some of the modes but not all of the modes.

19 Claims, 13 Drawing Sheets

(51) Int. Cl.
    *A61C 17/02*     (2006.01)
    *A61C 17/34*     (2006.01)
    *A61C 17/20*     (2006.01)

(52) U.S. Cl.
    CPC .......... *A61C 17/34* (2013.01); *A61C 17/3472* (2013.01); *A61B 5/4547* (2013.01); *A61C 17/02* (2013.01); *A61C 17/20* (2013.01); *A61C 17/222* (2013.01); *A61C 17/227* (2013.01); *A61C 17/3463* (2013.01); *A61C 17/3481* (2013.01)

(56) References Cited

U.S. PATENT DOCUMENTS

| | | | |
|---|---|---|---|
| 8,214,958 | B2 | 7/2012 | Pinyayev et al. |
| 8,512,040 | B2 | 8/2013 | Binner |
| 8,522,382 | B2 * | 9/2013 | Lee ................ A46B 5/0095 15/28 |
| 8,522,384 | B2 | 9/2013 | Leung |
| 9,310,333 | B2 | 4/2016 | Lavender |
| 9,811,636 | B2 | 11/2017 | Dykes et al. |
| 9,844,260 | B2 * | 12/2017 | Sayles ................ A46B 15/0042 |
| 10,314,493 | B2 | 6/2019 | Vermeulen |
| 2003/0156788 | A1 | 8/2003 | Henning |
| 2003/0194678 | A1 | 10/2003 | Viltro et al. |
| 2006/0183071 | A1 | 8/2006 | Hsuch |
| 2008/0060148 | A1 * | 3/2008 | Pinyayev ............. A61B 5/0088 15/4 |
| 2009/0132011 | A1 | 5/2009 | Altshuler et al. |
| 2011/0010876 | A1 | 1/2011 | Wahori et al. |
| 2012/0064480 | A1 | 3/2012 | Hegemann |
| 2013/0203008 | A1 | 8/2013 | Kressman et al. |
| 2014/0096332 | A1 | 4/2014 | Kitagawa et al. |
| 2016/0242652 | A1 | 8/2016 | Van Putten et al. |

FOREIGN PATENT DOCUMENTS

| | | |
|---|---|---|
| CN | 102106720 | 6/2011 |
| CN | 102131453 | 7/2011 |
| CN | 102488564 | 6/2012 |
| CN | 103348240 | 10/2013 |
| CN | 103445877 | 12/2013 |
| CN | 203354682 | 12/2013 |
| EP | 1101436 A2 | 5/2001 |
| IN | 202458761 | 10/2012 |
| JP | 2014133029 | 7/2014 |
| KR | 101338515 | 12/2013 |
| WO | 2003/101365 | 12/2003 |
| WO | 2006/098719 | 9/2006 |
| WO | 2012/005888 | 1/2012 |
| WO | 2014/097082 | 6/2014 |
| WO | 2014/097135 | 6/2014 |
| WO | 2015/056197 | 4/2015 |
| WO | 2015/059688 | 4/2015 |
| WO | 2015/082390 | 6/2015 |

* cited by examiner

ELECTRIC TOOTHBRUSH AND METHOD FOR OPERATING AN ELECTRIC TOOTHBRUSH

CROSS-REFERENCE TO RELATED APPLICATIONS

The present application is a divisional of U.S. patent application Ser. No. 15/735,367, filed Dec. 11, 2017, which is a national stage entry under 35 U.S.C. § 371 of PCT/US2016/036628, filed Jun. 9, 2016, which claims priority under 35 U.S.C. § 119 to Japanese Patent Application No. 2015-119561, filed Jun. 12, 2015, Japanese Patent Application No. 2015-119562, filed Jun. 12, 2015, and Japanese Patent Application No. 2015-122897, filed Jun. 18, 2015, the disclosures of which are incorporated herein by reference.

BACKGROUND

The present invention relates to an electric toothbrush and method for operating an electric toothbrush. A type of electric toothbrush that carries out tooth brushing by applying a brush oscillating at high speed to teeth is known. It has been proposed to provide on a brush unit of such electric toothbrush means for sensing a cavity of a tooth as well as plaque and tartar deposited on the tooth. Some electric toothbrushes are known that irradiate light against a tooth and detect the light reflected from the tooth using a light sensor to thereby sense a stain, such as plaque and tartar, on the tooth. These electric toothbrushes are used while toothpaste is on the brush unit. However, while toothpaste is on the surface of a tooth, light cannot be applied to the tooth to sense plaque and tartar deposited on the tooth. Thus, a need exists for an electric toothbrush that can improve the sensing accuracy of a stain on a tooth and optimize plaque removal.

BRIEF SUMMARY

The present invention may be directed, in one aspect, to an electric toothbrush comprising: a driving unit for driving a brush unit mounted on a main body; a light emitting module for emitting light from the brush unit; a reflected light detecting module for detecting reflected light of light emitted from the light emitting module; a stain sensing module for sensing a stain amount of a tooth based on an amount of the reflected light detected by the reflected light detecting module; a fluid spraying module for spraying fluid from the brush unit; and a fluid spray control unit for controlling spray timing of the fluid based on the amount of the reflected light detected by the reflected light detecting module.

In one aspect, the invention may be directed to a method for operating an electric toothbrush having a drive module for driving a brush unit mounted on a main body, including: a light emitting step for emitting light from the brush unit; a reflected light detecting step for detecting reflected light of the emitted light; a stain sensing step for sensing a stain amount of a tooth based on reflected light detected by the reflected light detecting step; a fluid spray step for spraying fluid from the brush unit; and a fluid spray control step for controlling the spray timing of the fluid based on the amount of reflected light detected by the reflected light detecting step.

In another aspect, the invention may be an electric toothbrush comprising: a body comprising a gripping part and a stem extending from the gripping part; a brush unit detachably coupled to the body, the brush unit having an outer surface including a front surface having a plurality of tooth cleaning elements extending therefrom; a motor located within the body and operably coupled to an eccentric shaft to oscillate the brush unit; a light emitting element configured to emit light from the brush unit; a light receiving element configured to receive reflected light of the light emitted from the light emitting element; a fluid dispensing system comprising a reservoir for storing a fluid, a fluid conduit extending from the reservoir to an outlet, and at least one of a pump and a valve for controlling dispensing of the fluid from the reservoir; a controller operably coupled to the motor, the light emitting element, the light receiving element, and the fluid dispensing system, the controller receiving data indicative of an amount of the reflected light received by the light receiving element; and wherein the controller controls operation of the fluid dispensing system based on the amount of the reflected light detected by the light receiving element.

In yet another aspect, the invention may be an electric toothbrush comprising: a body comprising a gripping part and a stem extending from the gripping part, the stem having an internal cavity, a first window that provides visibility from an outer surface of the stem into the internal cavity of the stem, and a first opening extending from the outer surface of the stem to the internal cavity of the stem; a brush unit detachably coupled to the body, the brush unit having an outer surface including a front surface having a plurality of tooth cleaning elements extending therefrom, a second window that provides visibility into an interior cavity of the brush unit, and a second opening extending from the outer surface of the brush unit to the interior cavity of the brush unit, the brush unit coupled to the body so that the first and second windows and the first and second openings are aligned; a motor located within the body and operably coupled to a controller to control operation of the motor; an eccentric shaft operably coupled to the motor and located at least partially within the internal cavity of the stem, a weight operably coupled to the eccentric shaft to oscillate the brush unit; a light emitting element located within the internal cavity of the stem and aligned with the first and second windows so that light emitted from the light emitting element passes through the first and second windows, the light emitting element operably coupled to the controller; a light receiving element located within the internal cavity of the stem and aligned with the first and second windows so that reflected light passes through the first and second windows to the light receiving element, the light receiving element operably coupled to the controller; a fluid dispensing system comprising a reservoir for storing a fluid, a fluid conduit extending from the reservoir to the first opening in the stem, and at least one of a pump and a valve operably coupled to the controller for controlling dispensing of the fluid from the reservoir; and wherein the controller controls operation of the fluid dispensing system based on an amount of the reflected light detected by the light receiving element.

In still another aspect, the invention may be a method for operating an electric toothbrush having a drive module for driving a brush unit mounted on a main body, the method comprising: emitting light from the brush unit towards a tooth; detecting reflected light of the emitted light that reflects off of the tooth; and spraying fluid from the brush unit based on an amount of the reflected light detected.

In a further aspect, the invention may be an electric toothbrush comprising: a driving portion that performs a first driving that oscillates a brush unit in a first direction that is a pressing direction of a plurality of tooth cleaning elements provided on the brush unit and a second driving that oscillates the brush unit in a second direction that is different from the first direction; a fluid spraying unit that sprays a fluid from the brush unit; and wherein the driving portion carries out the first driving while the fluid is being sprayed from the fluid spraying unit.

In a still further aspect, the invention may be a method for electric toothbrush operation comprising: a driving step that performs a first driving that oscillates a brush unit coupled to a main body portion of the electric toothbrush in a first direction that is a pressing direction of a plurality of tooth cleaning elements provided on the brush unit and a second driving that oscillates the brush unit in a second direction that is different from the first direction; a fluid spraying step that sprays a fluid from the brush unit; and wherein the driving step carries out the first driving while the fluid is being sprayed according to the fluid spraying step.

In another aspect, the invention may be an electric toothbrush comprising: a body comprising a gripping part and a stem extending from the gripping part; a brush unit detachably coupled to the body and having a plurality of tooth cleaning elements extending therefrom; a drive assembly located in the body and configured to oscillate the brush unit, wherein the drive assembly is operably coupled to a controller to alternate operation of the drive assembly between at least: (1) a first mode wherein the drive assembly oscillates the brush unit in a first direction; and (2) a second mode wherein the drive assembly oscillates the brush unit in a second direction that is different than the first direction; a fluid dispensing system for dispensing a fluid, the fluid dispensing system operably coupled to the controller to control operation of the fluid dispensing system; and wherein when the fluid is being dispensed by the fluid dispensing system, the drive assembly only operates in the first mode.

In one aspect, the invention may be an electric toothbrush comprising: a drive module for selectively performing a first drive for oscillating a brush unit installed on a main body in a first direction that is a pressing direction of a plurality of tooth cleaning elements provided on the brush unit and a second drive for oscillating the brush unit in a second direction that is different from the first direction; a light emitting module for emitting light from the brush unit; a reflected light detector for detecting reflected light of the light emitted from the light emitting module; a plaque detector for detecting plaque based on the reflected light detected by the reflected light detector; a liquid spray part for spraying liquid from a portion of the brush unit that is surrounded by the plurality of tooth cleaning elements; and a liquid spray controller for controlling a spray timing of the liquid; wherein the liquid spray controller sprays the liquid when the amount of plaque detected by the plaque detector exceeds a threshold; and wherein the drive module stops the first drive and performs only the second drive while the liquid is being sprayed.

In still another aspect, the invention may be an operating method of an electric toothbrush comprising a light emitting module for emitting light from a brush unit having a plurality of tooth cleaning elements installed on the electric toothbrush, a reflected light detector for detecting reflected light of the light emitted from the light emitting module, and a liquid spray part for spraying liquid from a portion surrounded by the plurality of tooth cleaning elements from the brush unit, the method comprising: a drive step for selectively performing a first drive for oscillating the brush unit installed on a main body in a first direction, which is the direction of pressing the plurality of tooth cleaning elements provided on the brush unit and a second drive for oscillating the brush unit in a second direction, which is different from the first direction; a plaque detection step for detecting plaque based on the reflected light detected by the reflected light detector; and a liquid spray control step for spraying the liquid when the amount of plaque detected during the plaque detection step exceeds a threshold; and wherein within the drive step, the first drive is stopped and only the second drive is performed while the liquid is being sprayed.

In yet another aspect, the invention may be an electric toothbrush comprising: a body comprising a gripping part and a stem extending from the gripping part; a brush unit detachably coupled to the body and having a plurality of tooth cleaning elements extending therefrom; a drive assembly located in the body and configured to oscillate the brush unit, wherein the drive assembly is operably coupled to a controller to alternate operation of the drive assembly between at least: (1) a first mode wherein the drive assembly oscillates the brush unit in a first direction; and (2) a second mode wherein the drive assembly oscillates the brush unit in a second direction that is different than the first direction; a light emitting element operably coupled to the controller and configured to emit light from the brush unit; a light receiving element operably coupled to the controller and configured to receive reflected light of the light emitted from the light emitting element, the controller determining an amount of plaque based on an amount of the reflected light received by the light receiving element; and a fluid dispensing system for dispensing a fluid, the fluid dispensing system operably coupled to the controller, the controller initiating the fluid dispensing system to dispense the fluid when the amount of plaque exceeds a threshold; and wherein when the fluid is being dispensed by the fluid dispensing system, the drive assembly only operates in the second mode.

In still another aspect, the invention may be an electric toothbrush comprising: a body comprising a gripping part and a stem extending from the gripping part; a brush unit detachably coupled to the body and having a plurality of tooth cleaning elements extending therefrom; a drive assembly located in the body and configured to oscillate the brush unit, wherein the drive assembly is operably coupled to a controller to alternate operation of the drive assembly between at least: (1) a first mode wherein the drive assembly oscillates the brush unit in a first direction; and (2) a second mode wherein the drive assembly oscillates the brush unit in a second direction that is different than the first direction; a light emitting element operably coupled to the controller and configured to emit light from the brush unit; a light receiving element operably coupled to the controller and configured to receive reflected light of the light emitted from the light emitting element, the controller determining an amount of plaque based on an amount of the reflected light received by the light receiving element; and a fluid dispensing system for dispensing a fluid, the fluid dispensing system comprising a tank for storing the fluid, the fluid dispensing system operably coupled to the controller, wherein the controller is configured to identify the fluid as a type of fluid and initiate the fluid dispensing system to dispense the fluid when the amount of plaque exceeds a threshold; and wherein when the fluid is being dispensed by the fluid dispensing system and the fluid is water, the drive assembly only operates in the first mode; and wherein when the fluid is being dispensed by the fluid dispensing system and the fluid is not water, the drive assembly only operates in the second mode.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
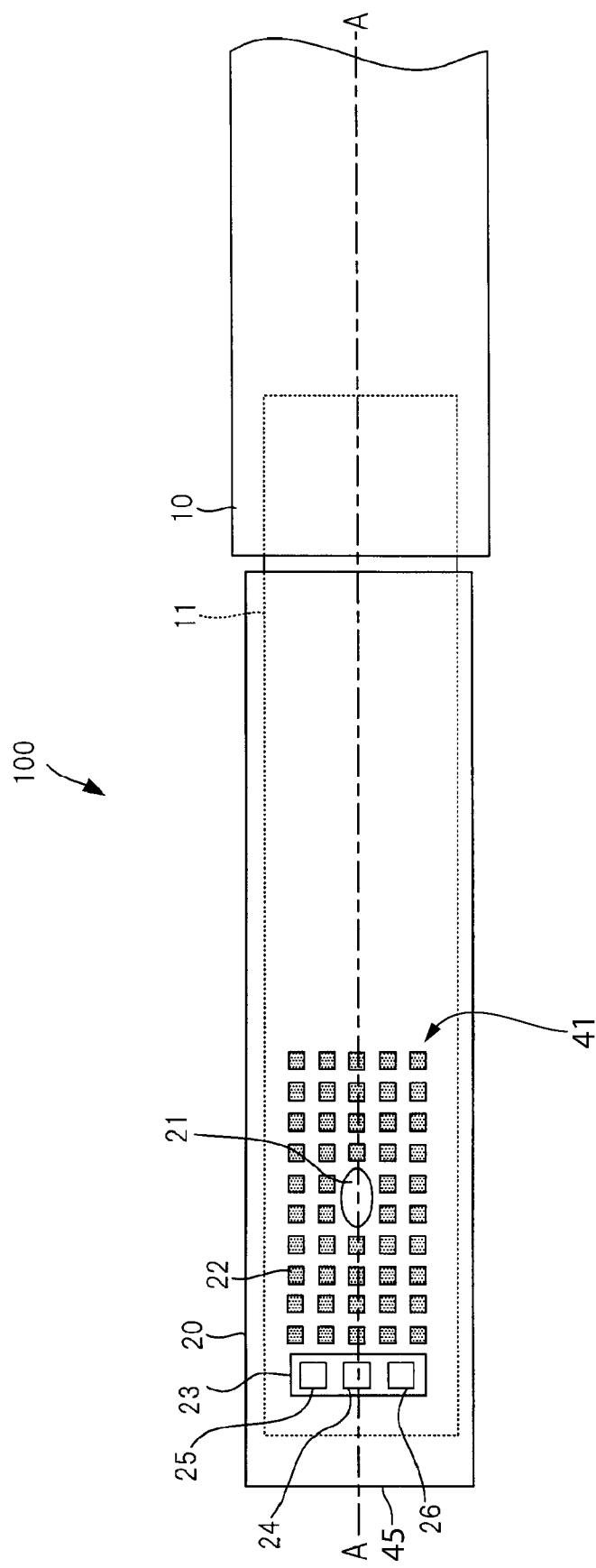
FIG. 1 is a top view of an electric toothbrush in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 2:
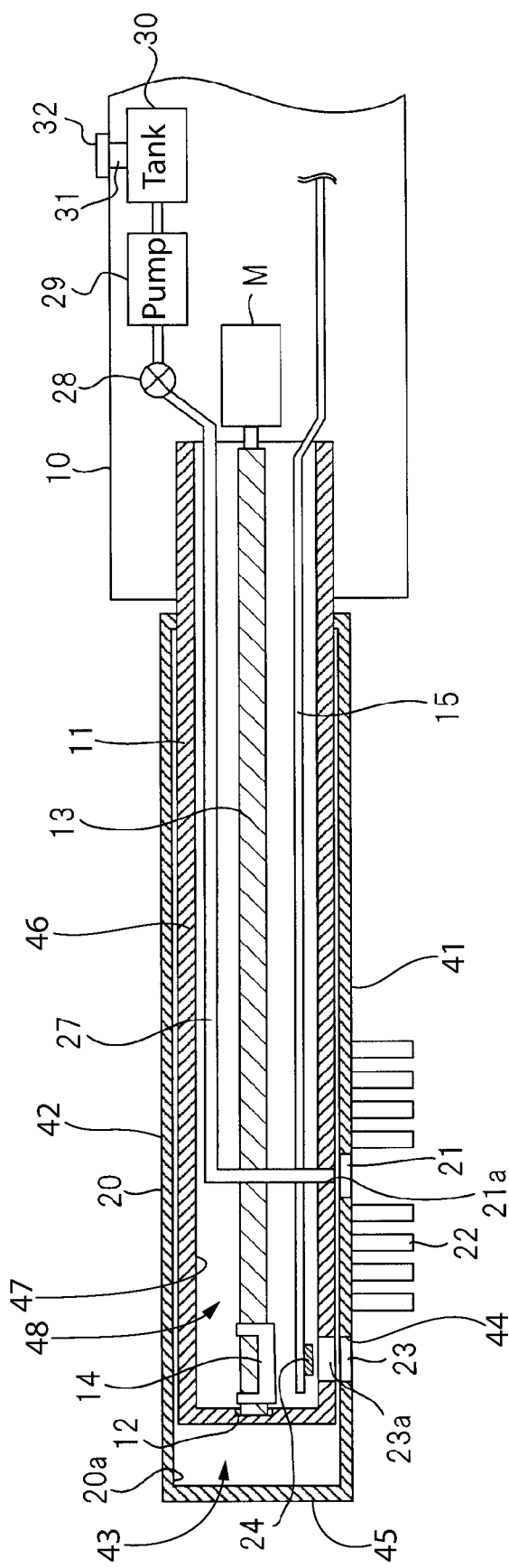
FIG. 2 is a schematic cross sectional view taken along line A-A in FIG. 1.

Referring to FIGS. 1 and 2 concurrently, an electric toothbrush 100 (also referred to herein as an oral care implement or a powered toothbrush in some embodiments) will be described in accordance with an embodiment of the present invention. FIG. 1 is a planar view illustrating a schematic configuration of the electric toothbrush 100 viewed from the brush pressing direction (the direction that a user presses onto tooth cleaning elements during use), for describing one embodiment of the present invention. FIG. 2 is a cross-sectional view taken along line A-A of FIG. 1.

The electric toothbrush 100 includes a gripping part 10 that includes a battery and an electric control system therein, as well as a main body having a stem 11 fixed to the gripping part 10, and a brush unit 20 that can be detached from the stem 11. The stem 11 extends from the gripping part 10 and forms the portion of the electric toothbrush 100 that the brush unit 20 may be coupled to. Specifically, the brush unit 20 comprises a cylindrical housing that defines an interior cavity 43 having a closed distal end 20a. The brush unit 20 may be coupled to the stem 11 by inserting the stem 11 into the interior cavity 43 of the brush unit. The brush unit 20 may be repetitively coupled to and detached from the stem 11 as necessary or desired. The brush unit 20 and the stem 11 may also include corresponding structures that facilitate locking the brush unit 20 to the stem 11 (a boss and a corresponding notch, an indent and a corresponding detent, or the like). Thus, the gripping part 10 and the stem 11 may be reused with different brush units 20 having different structural arrangements to achieve different purposes. Furthermore, the brush units 20 may be replaced when the tooth cleaning elements thereon are worn or splayed over time. This saves a user costs because the portion of the electric toothbrush 100 that includes the circuitry may be reused while the brush unit 20 which is a simple and cheap component may be replaced. The brush unit 20 may be referred to herein and in the art as a refill head.

The brush unit 20 includes a front surface 41 and an opposite rear surface 42. In certain embodiments the brush unit 20 may comprise a head portion and a sleeve portion. Furthermore, the brush unit 20 includes a plurality of tooth cleaning elements 22 extending from the front surface 41 (particularly of the head portion). The plurality of tooth cleaning elements 22 are depicted in various aligned columns and rows, although the invention is not to be so limited. The number, pattern, configuration, and structure of the tooth cleaning elements 22 are not to be limited by the exemplary embodiments illustrated in all embodiments. In certain embodiments, the tooth cleaning elements 22 are formed by a plurality of bristles that are bundled together into tufts that are then coupled to the head portion of the brush unit 20. The tooth cleaning elements 22 may be coupled to the head using staple technology, anchor-free tufting technologies, in-mold tufting technologies, or any other technology now known or later discovered. The tooth cleaning elements 22 may include bristles alone, bristles in combination with lamella formed of an elastomeric material, only bristles formed of an elastomeric material, or the like.

The invention is not to be particularly limited by the specific details of the bristles unless specifically claimed as such. As discussed above, in certain embodiments the brush unit 20 may be detachable from the stem 11 and replaceable as needed when the tooth cleaning elements 22 thereon become frayed from use.

The brush unit 20 also includes a hole 21 that permits a liquid to be sprayed therethrough and a transparent window 23 that permits light to be emitted therethrough. Specifically, in the exemplified embodiment the hole 21 is formed into the front surface 41 of the brush unit 20 and forms a passageway from the ambient environment into the interior cavity 43. Furthermore, the hole 21 is fluidly coupled to a fluid conduit 27 so that fluid can flow through the fluid conduit 27 and out the hole 21 as described in more detail below. In the exemplified embodiment the hole 21 is positioned in a central region of the brush unit 20 surrounded by the tooth cleaning elements 22. However, the position of the hole 21 is an example, and is not limited to the position illustrated in FIG. 1. Thus, the hole 21 may be located at other positions along the brush unit 20, including other positions on the front surface 41 of the brush unit 20 and even on the rear surface 42 of the brush unit 20 in other embodiments. The hole 21 may be disposed so that the liquid can be emitted in the direction the tooth cleaning elements 22 extend from the brush unit 20 (i.e., perpendicular to the front surface 41 of the brush unit 20). Alternatively, the hole 21 may be arranged so that the liquid can be sprayed at an oblique angle relative to the front surface 41 of the brush unit 20.

In the exemplified embodiment, the brush unit 20 includes a second hole 44 for retaining the transparent window 23. Specifically, the transparent window 23 is formed by fitting a translucent member such as a transparent resin or transparent glass to the second hole 44 provided in the housing of the brush unit 20. In the exemplified embodiment, the transparent window 23 is located on the front surface 41 of the brush unit 20 (i.e., the same surface from which the tooth cleaning elements 22 extend). Furthermore, in the exemplified embodiment the transparent window 23 is located along a distal portion of the brush unit 20. Specifically, in the exemplified embodiment the tooth cleaning elements 22 form a bristle field, and the transparent window 23 is located external to the bristle field and between the bristle field and a distal-most end 45 of the brush unit 20. Of course, the invention is not to be so limited in all embodiments and the transparent window 23 may be located within the field of tooth cleaning elements 22 or at any other desired location along the brush unit 20 in other embodiments. Thus, the invention is not to be particularly limited by the position of the transparent window 23 unless specifically claimed as such. Stated another way, the position of the transparent window 23 is an example, and is not limited to the position illustrated in FIG. 1.

As will be described in more detail below, the window 23 is positioned adjacent to a light source so that light from the light source may emit through the window 23. The light source and the window 23 may be disposed so that the light can be emitted in the direction the tooth cleaning elements 22 extend from the front surface 41 of the brush unit 20 (i.e., perpendicular to the front surface 41 of the brush unit 20). In other embodiments, the window 23 may be disposed so that the light can be emitted in a direction that is at an oblique angle relative to the front surface 41 of the brush unit 20.

The stem 11 is configured with a cylindrical housing in which the tip end (end of the opposite side of the gripping part 10 side) is closed. The stem 11 includes a bearing 12 formed on the tip end therein, an eccentric shaft 13 in which one end is inserted into the bearing 12, a weight 14, substrate 15, a light emitting element 24 formed on the substrate 15, a light receiving element 25 and a light receiving element 26 (see FIG. 1) formed on the substrate 15, a transparent window 23a provided in the housing, and the fluid conduit 27. In certain embodiments, the light emitting element 24 and the light receiving elements 25, 26, alone or in combination with a controller, may be collectively referred to as a tooth stain or plaque detection system.

The gripping part 10 includes a valve 28 connected with the fluid conduit 27 extending from inside the stem 11, a pump 29 connected to the valve 28, a tank 30 connected to the pump 29, a liquid supply opening 31 for pouring liquid in the tank 30, a cap 32 for closing the liquid supply opening 31, and a motor M linked with the eccentric shaft 13 in the stem 11. Although the exemplified embodiment illustrates the tank 30, in other embodiments the tank 30 may be omitted and the fluid conduit 27 may be coupled directly to a source of fluid rather than to the tank 30. The tank 30, the fluid conduit 27, the pump 29, and/or the valve 28 may be collectively referred to herein as a fluid spraying unit or a fluid dispensing system.

The other end of the eccentric shaft 13 is linked to a rotary shaft of the motor M built in the gripping part 10. By rotating the rotary shaft of the motor M, the eccentric shaft 13 rotates. The weight 14 is fixed to the eccentric shaft 13 in the vicinity of the bearing 12. Due to this weight 14, the center of gravity of the eccentric shaft 13 is shifted from the center of rotation. Note that a minute clearance is provided between the eccentric shaft 13 and the bearing 12. Although the eccentric shaft 13 rotates along with the rotation of the rotary shaft of the motor M, since the center of gravity of the eccentric shaft 13 is shifted due to the weight 14, a motion of turning about the center of rotation is carried out. Thus, the entire eccentric shaft 13 bends, and the stem 11 as well as the brush unit 20 installed therein, oscillate at a high speed. Specifically, when the motor M is powered on and rotating, the eccentric shaft 13 rotates and due to the offset nature of the weight 14 (also referred to herein as an eccentric), the brush unit 20 oscillates. Thus, powering the motor M results in the brush unit 20 oscillating, which enhances cleaning of a user's teeth. The combination of the motor M, the eccentric shaft 13, and the weight 14 may be referred to collectively herein as a drive unit or a drive assembly in some embodiments. Thus, the components that work together to create oscillation in the brush unit 20 may be referred to as the drive unit or drive assembly.

Thus, in cases of the drive principle in which the brush unit 20 is oscillated due to the turning motion of the eccentric shaft 13, the brush unit 20 may oscillate two-dimensionally in a plane perpendicular (parallel to the pressing direction of the tooth cleaning elements 22) to the rotary shaft of the motor M. Note that, the pressing direction of the tooth cleaning elements 22 coincides with the direction in which each tooth cleaning elements 22 is extending. Thus, the pressing direction of the tooth cleaning elements 22 is the direction perpendicular to the front surface 41 of the brush unit 20.

With the electric toothbrush 100, the entirety of the oscillating part (stem 11 and brush unit 20) has a resonance point (resonance frequency), and can switch operations (or modes) between a first operation or mode in which the stem 11 and brush unit 20 oscillate in the pressing direction of the tooth cleaning elements 22 and a second operation or mode in which the stem 11 and brush unit 20 oscillate in a direction that is different from the direction of oscillation in the first operation or mode. Thus, in the second operation or mode the brush unit 20 may oscillate in a direction that intersects the pressing direction of the tooth cleaning elements 22. The second operation or mode may be in a plane perpendicular to the rotary shaft of the motor M (i.e., side-to-side in a direction of the lateral sides of the brush unit 20) or in a plane parallel to the rotary shaft of the motor M (in a back-and-forth direction in a direction towards and away from the distal-most end 45 of the brush unit 20. In some embodiments, the mode or operation of the electric toothbrush 100 may be changed between the first and second operations/modes by controlling the rotary speed of the motor M, although other techniques for alternating between the modes may also be used.

As illustrated in FIG. 2, the stem 11 comprises a housing 46 having an inner surface 47 that defines a cavity 48. The shaft 13 is positioned within the cavity 48 of the stem 11. Furthermore, the stem 11 comprises a transparent window 23a in a location facing or adjacent to the transparent window 23 of the housing of the brush unit 20. The transparent window 23a of the stem 11 may be formed of substantially the same size as the transparent window 23 of the brush unit 20. The transparent windows 23, 23a cooperate to permit light from the light emitting element 24 to pass through both of the transparent windows 23, 23a so that the light may be emitted from the electric toothbrush 100 to a user's teeth and other oral surfaces. The transparent window 23a is formed by fitting a translucent member such as a transparent resin or transparent glass and the like in a hole formed into the housing 46 of the stem 11.

The light emitting element 24 illustrated in FIG. 1, the light receiving element 25, and the light receiving element 26, are disposed on the substrate 15 in a position opposite the transparent window 23a. Thus, the light emitting element 24 and the light receiving elements 25, 26 are visible through, and are capable of emitting light and receiving light, respectively, through the windows 23, 23a. The light emitting element 24 and the windows 23, 23a are generally positioned and oriented to permit light from the light emitting element 24 to be emitted towards or onto a user's teeth. The light receiving elements 25, 26 and the windows 23, 23a are generally positioned and oriented to permit light that is reflected off of the teeth to be emitted back to the light receiving elements 25, 26. This functionality will be described in more detail below.

Although the above states that the light receiving elements 25, 26 are configured to receive light that is reflected off of the teeth, it should be appreciated that the light is not always reflected off of the teeth as that term is commonly defined. Rather, in certain instances the light may be fluoresced by the teeth. Specifically, reflectance is when light is not absorbed, but is redirected back and fluorescence is when light is absorbed, and then re-emitted at a different wavelength. Thus, in certain instances the light emitted at the teeth is fluoresced back towards the light receiving elements 25, 26 rather than being reflected back towards the light receiving elements 25, 26. Thus, as used herein, the term reflect will include solely reflectance, solely fluorescence, and combinations of reflectance and fluorescence. Each iteration of the term "reflect," "reflected," "reflectance," or similar in the specification and the claims should be understood to include light that is reflected and/or fluoresced.

The light emitting element 24 may comprise an LED (Light Emitted Diode) or a laser diode and the like. The light emitting element 24 is not to be limited by any particular type of light source and the above are merely non-limiting examples. The light emitting element 24 may in some embodiments emit a light in the blue wavelength range (hereinafter referred to as B light). This may be desirable because B light is generally understood to be capable of sensing a stain (plaque, tartar and the like) on teeth. The B light emitted from the light emitting element 24 passes through the transparent window 23a and the transparent window 23, and is emitted outside of the brush unit 20 and onto the user's teeth during use of the electric toothbrush 10. The light emitting element 24, the transparent window 23a and the transparent window 23 may collectively function as a light emitting module for emitting light from the brush unit 20.

The light receiving element 25 and the light receiving element 26 are configured respectively by a photoelectric conversion element such as a photo diode that converts the light to an electrical signal. The light receiving element 25 is configured to detect light in the red wavelength range (hereinafter referred to as R light). Furthermore, the light receiving element 25 is configured by a photoelectric conversion element to output a signal corresponding to the amount of R light detected. This signal may be received by a controller for further processing. The light receiving element 25 is configured as a combination of a color filter that transmits R light and a photo diode that has sensitivity in visible light, or as a photo diode and the like that can only detect R light.

The light receiving element 26 is configured to detect light in the green wavelength range (hereinafter referred to as G light). Furthermore, the light receiving element 26 is configured by a photoelectric conversion element to output a signal corresponding to the amount of G light detected. This signal may be received by a controller for further processing. The light receiving element 26 is configured as a combination of a color filter that transmits G light and a photo diode that has sensitivity in visible light, or as a photo diode and the like that can only detect G light. The light receiving elements 25, 26 are similar except with respect to the wavelength of light receive thereby.

During use, the light emitting element 24 emits B light through the windows 23, 23a and onto the user's teeth. When the B light contacts plaque adhering to the tooth, the R light becomes excited in the plaque. In other words, when the B light contacts plaque (i.e., plaque adhered to the tooth), R light is generated as the reflected light of the B light. In certain embodiments, the B light is absorbed by the plaque and re-emitted as the R light (i.e., fluoresced). In addition, when the B light contacts a portion of the tooth without plaque (i.e., an exposed portion of the tooth), the G light is added to the reflected portion of the B light in this portion. In certain embodiments, the B light is absorbed by the exposed portion of the tooth and re-emitted as G light (i.e., fluoresced). As noted above, the term "reflect" as used herein includes reflectance, fluorescence, and combinations thereof. In other words, the G light is generated as one part the reflected (or fluoresced) light of the B light. Sated another way, the B light is emitted at the user's tooth or teeth. The B light is then reflected (or fluoresced) from the user's teeth as both R light and G light. Thus, the reflected (or fluoresced) light has an R light component for portions of the B light that are reflected (fluoresced) from portions of the tooth that have plaque thereon and a G light component for portions of the B light that are reflected (fluoresced) from portions of the tooth that have no plaque thereon (i.e., exposed portions of the tooth).

To state succinctly, the light receiving element 25 is provided for detecting/receiving R light that is generated when the B light emitted from the light emitting element 24 contacts plaque, tartar, or other stain. The light receiving element 26 is provided for detecting G light generated when the B light emitted from the light emitting element 24 contacts an exposed portion of the tooth that is free of plaque, tartar, or other stain. The light receiving element 25 and the light receiving element 26 function as a reflecting/fluorescing light detecting module that detects reflected/fluoresced light of the B light emitted from the light emitting module. In some embodiments, the light receiving elements 25, 26 may be a single light receiving element capable of receiving and distinguishing between the R light and the G light. Thus, as used herein the phrase light receiving element may denote a single light receiving element that is configured to receive both the R light and the G light or multiple light receiving elements for separately receiving the R light and the G light, respectively.

The substrate 15 may be any type of electrical substrate that can operably power the light emitting element 24 and the light receiving elements 25, 26. In some embodiments, the substrate 15 may be a flexible substrate, although the invention is not to be so limited in all embodiments and the substrate 15 may be any other type of substrate as desired. The substrate 15 is electrically connected to the light emitting element 24, the light receiving element 25 and the light receiving element 26. The substrate 15 extends to the inside part of the gripping part 10, and the wiring formed in the substrate 15 is electrically connected to a controller 50 (see FIG. 3) to be described later, that is built into the gripping part 10. In this manner, the controller 50 controls operation of the light emitting element 24 and the light receiving elements 25, 26. Specifically, the controller 50 may control the on/off status of the light emitting element 24 and may permit the transfer and storage of signals from the light receiving elements 25, 26 regarding amounts of R and G light received to facilitate other functions of the electric toothbrush 100 described herein.

The tank 30 forms a reservoir that retains a liquid introduced therein from the liquid supply opening 31. Specifically, a user or manufacturer may open the supply opening 31 by removing the cap 32. The user or manufacturer may then pour or otherwise introduce a desired liquid into the tank 30. The liquid may be any desired liquid, including without limitation water, mouthwash, oral care agents that have a desired benefit, and the like. The invention is not to be specifically limited by the particular liquid used unless specifically recited as such in the claims.

The pump 29 pumps the liquid retained by the tank 30 and supplies it to the valve 28. Thus, the pump 29 moves the liquid from the tank 30 along a conduit to the valve 28. The pump 29 may be any type of pump capable of achieving this function. The valve 28 is fluidly coupled to the base end of the fluid conduit 27 extending from the inside of the stem 11, and controls the supply amount and supply pressure of the liquid supplied to the fluid conduit 27, as well as the supply timing of the liquid to the fluid conduit 27. In that regard and as discussed in more detail below with reference to FIG. 3, the valve 28 is operably coupled to the controller 50 so that the controller 50 may provide instructions to the valve 28 regarding the amount of the liquid to be supplied, the pressure of the liquid to be supplied, and the time period during which to supply the liquid. This can also be achieved via the pump 29 in communication with the controller 50 rather than or in addition to the valve 28.

The fluid conduit 27 is configured as a tubular member that the liquid can pass through. The fluid conduit 27 may be formed of any desired material so long as it is impermeable to fluid so that the fluid remains within the fluid conduit 27 as it passes therethrough. In the housing 46 of the stem 11, a hole 21a is provided in a portion opposite and facing the hole 21 of the brush unit 20. Specifically, the hole 21a in the housing 46 of the stem 11 is positioned to be in alignment with the hole 21 of the brush unit 20 so that the holes 21, 21a collectively form an outlet of the fluid dispensing system. The tip end of the fluid conduit 27 is fitted in the hole 21a. The tip end of the fluid conduit 27 may be pressed against the hole 21, fitted within the hole 21, extending through the hole 21, or the like in various embodiments. With this configuration, the liquid sprayed from the tip end of the fluid conduit 27 passes through the hole 21 of the brush unit 20 and is sprayed to the outside of the brush unit 20. When the electric toothbrush 100 is being used, the brush unit 20 is within the user's mouth and the fluid being sprayed from the fluid conduit 27 will be sprayed into the user's mouth. The benefits of this, which include: (1) clearing dentifrice or the like away from the teeth to better enable the light from the light emitting element 24 to contact and be reflected/fluoresced off of the tooth surfaces; and (2) cleaning plaque and tartar from the teeth, will be described in more detail below.

The pump 29, valve 28, fluid conduit 27, hole 21a, and hole 21 collectively function as a fluid spray module or a fluid dispensing system for spraying a fluid from the brush unit 20. By changing the cross sectional shape of the hole 21, it is possible to change the spray direction and spray pattern of the liquid sprayed from the brush unit 20. In some embodiments, the spray direction is in the direction in which the angle formed with the pressing direction is less than 90 degrees, and it is most preferable for the pressing direction (extending direction of the tooth cleaning elements 22) of the tooth cleaning elements 22 to be the same.

Figure 3:
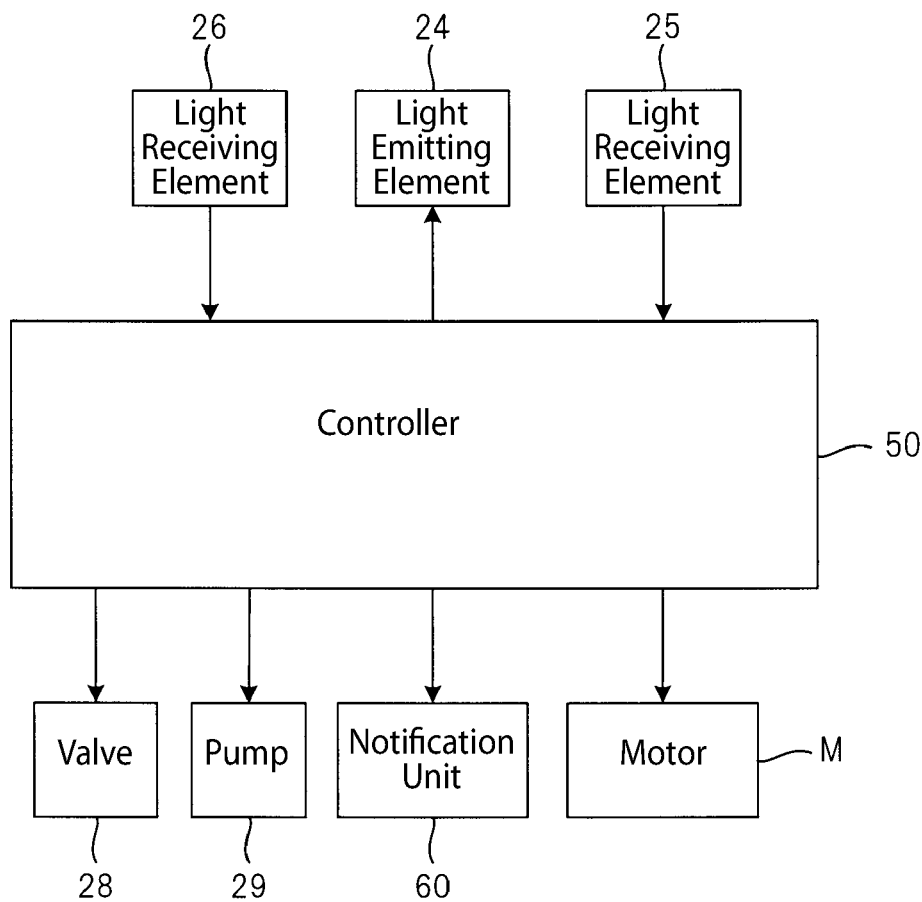
FIG. 3 is a block diagram illustrating an internal configuration of a main body of the electric toothbrush of FIG. 1.

FIG. 3 is a block diagram illustrating an electrical configuration of the main body of the electric toothbrush 100 illustrated in FIG. 1. The main body of the electric toothbrush 100 includes the motor M, a notification unit 60, the controller 50, the pump 29, and the valve 28. As shown in FIG. 3, each of the valve 28, the pump 29, the notification unit 60, the motor M, the light emitting element 24, and the light receiving elements 25, 26 are operably coupled to the controller 50. As a result, the controller 50 may communicate with, provide instructions to, and receive information/signals from each of the aforementioned components. For example, the controller 50 may control when the motor M powers on and off and the speed at which the motor M should rotate, which affects the oscillation of the brush unit 20 as described above. Furthermore, the controller 50 may control when the valve 28 and pump 29 operate and when the light emitting element 24 emits light. The controller 50 may also receive signals from the light receiving elements 25, 26 regarding the amounts of R and G light received by the light receiving elements 25, 26. The controller 50 may then process that information/data regarding the R and G light to provide instructions regarding operation of the valve 28, pump, 29, motor M, and notification unit 60 as described in more detail below based on the amount of R and G light received.

The controller 50 functions as a drive module that drives the brush unit 20 mounted on the stem 11, by controlling the motor M. The controller 50 selectively carries out a first drive (or a first mode) for oscillating the brush unit 20 in a first direction, which may be an up-down oscillation in the pressing direction of the tooth cleaning elements 22, and a second drive (or a second mode) for oscillating the brush unit 20 in a second direction that is different than the first direction. The second direction may be a direction intersecting the pressing direction of the tooth cleaning elements 22 in the plane perpendicular to the rotary shaft of the motor M. Alternatively, the second direction may be a direction intersecting the pressing direction of the tooth cleaning elements 22 in a plane parallel to the rotary shaft of the motor M. The controller 50 may be configured to oscillate the brush unit 20 so that the second direction is an arbitrary direction and it may be in a plane perpendicular to the first direction. The controller 50 carries out switching of the first drive and second drive by changing the rotational speed of the rotary shaft of the motor M. Thus, rotation of the rotary shaft of the motor M at a first speed results in the first drive or mode and rotation of the rotary shaft of the motor at a second speed results in the second drive or mode.

During operation of the electric toothbrush 100, the controller 50 may alternate between carrying out the first and second drives or modes (i.e., causing the brush head 20 to oscillate in the first direction and the second direction). The controller 50 may alternate between the first and second drives or modes based on a preset timing (i.e., 10 seconds in the first drive direction followed by 10 seconds in the second drive direction), based on a location of the brush unit 20 in the user's mouth, based on a direction of movement of the brush unit 20 within the user's mouth, or the like. By automatically switching the oscillating direction of the brush unit 20, since the bristles of the tooth cleaning elements 22 will contact the teeth and oral surfaces from various angles with regards to the treatment section, it is possible to obtain a better plaque removal effect compared to a single direction of brushing. Note that the driving method of the stem 11 is not particularly limited by the controller 50. For example, the controller 50 may only carry out the first drive (mode), or the controller 50 may only carry out the second drive (mode). Thus, in some embodiments the electric toothbrush 100 may only be capable of operating in a single mode rather than the dual mode as disclosed herein. Furthermore, in still other embodiments the electric toothbrush 100 may be configured to operate in more than two drives or modes.

The controller 50 may also drive the light emitting element 24 via the substrate 15, thereby controlling the emitting of the B light from the light emitting element 24. Thus, the controller 50 may determine the appropriate timing for emitting light from the light emitting element 24, as described in more detail below.

The controller 50 carries out a stain sensing process for sensing the amount of stain on a tooth such as plaque and tartar adhered to the tooth, based on reflected light detected by the light receiving element 25. The stain sensing process is carried out by a well-known method based on the amount of light (detection signal level) of R light detected by the light receiving element 25. In this regard, the controller 50 functions as a stain sensing module.

The controller 50 controls spray timing of the liquid sprayed from the hole 21, and the spray amount and spray pressure of the liquid, by controlling the valve 28 and pump 29 based on the amount of light of G light detected by the light receiving element 26 and the amount of light of the R light detected by the light receiving element 25. In this regard, the controller 50 functions as a fluid spray control unit.

The notification unit 60 comprises a device such as a speaker or a LED (Light Emitting Diode), and notifies the user of the electric toothbrush 100 when specific conditions are or are not met. The notification unit 60 notifies the user by playing a sound or flashing the LED according to instructions from the controller 50. For example, in one embodiment the content to be notified is the stain amount of the teeth calculated by the controller 50. For example, the notification unit 60 notifies the stain amount of the tooth by flashing the green LED when the stain amount is very small, and flashing the red LED when the stain amount is large, and thus supports effective brushing of teeth.

Figure 4:
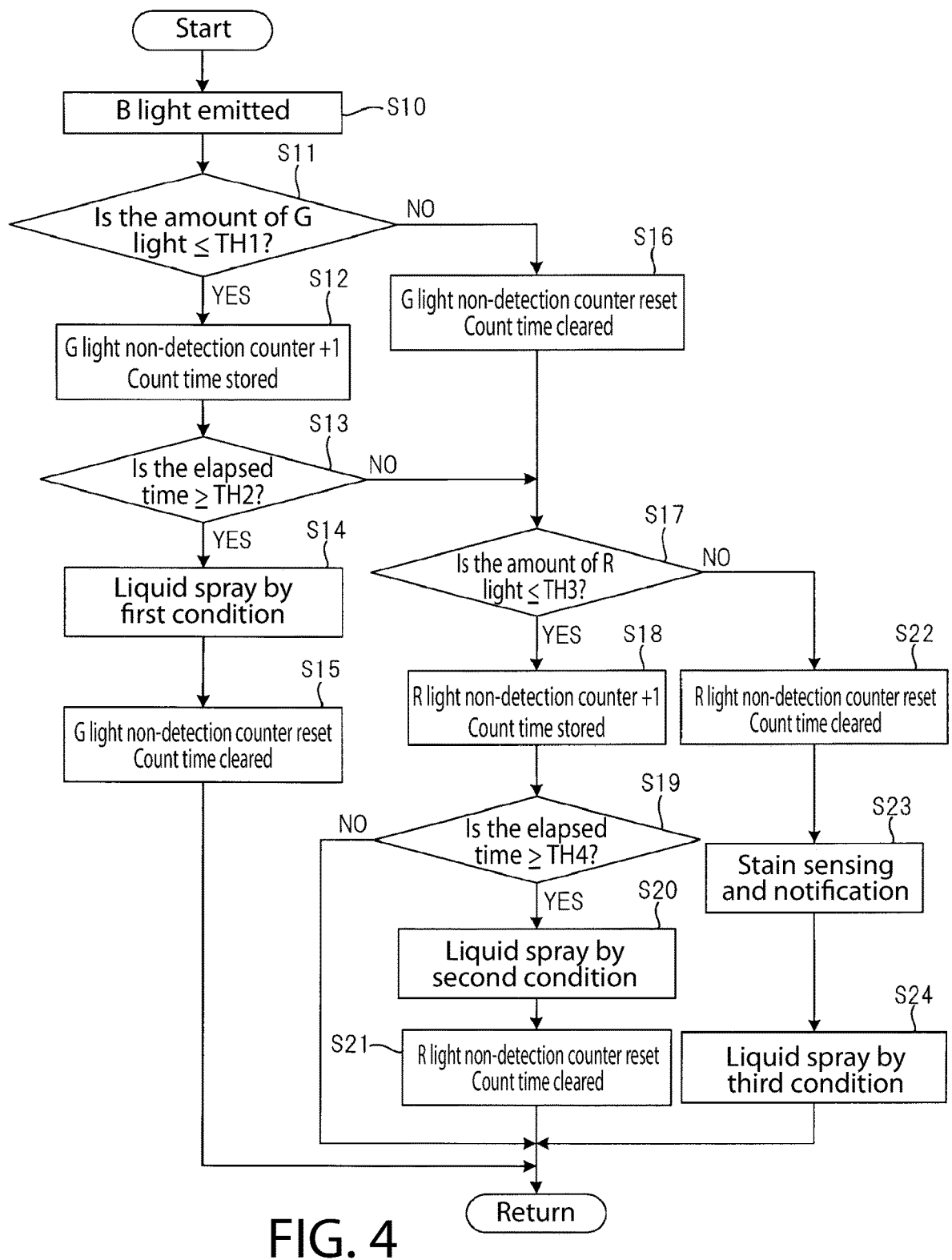
FIG. 4 is a flowchart for describing the operation of the electric toothbrush of FIG. 1.

FIG. 4 is a flowchart for describing the operation of the electric toothbrush 100 illustrated in FIG. 1. When the brushing start operation is performed by the power of the electric toothbrush 100 being turned on, the controller 50 starts the control for alternating carrying out the first drive and second drive in accordance with pre-programmed instructions. Thus, the brush unit 20 pressed against the teeth repeats alternating oscillating in the first direction and oscillating in the second direction, and the plaque adhered to the teeth is removed by the tooth cleaning elements 22. The brush unit 20 may oscillate for identical time periods in both the first direction and the second direction, or it may oscillate longer in one of the first and second directions than the other. The specific program that the controller 50 follows in instructing oscillation of the brush unit 20 may be modified as desired.

In one embodiment, the controller 50 causes the light emitting element 24 to emit light at a predetermined timing while alternating between the first drive (mode) and the second drive (mode). However, as discussed below the controller 50 may only cause the light emitting element 24 to emit light during one of the first drive or the second drive in some embodiments. The B light emitted from the light emitting element 24 is emitted to the outside of the brush unit 20 through the transparent window 23 (Step S10). The B light contacts and reflects off of the user's teeth as R light (when the B light contacts plaque) and G light (when the B light contacts exposed tooth surfaces). The light receiving elements 25, 26 receive the R and G light, respectively, almost immediately after the light emitting element 24 begins to emit the B light. Upon receiving the R and G light, the light receiving elements 25, 26 transmit signals to the controller indicative of the amounts of R and G light received.

The controller 50 then determines whether or not the amount of light of G light detected by the light receiving element 26 (detection signal level of the light receiving element 26) is less than or equal to a first threshold TH1 (Step S11). The first threshold is a predetermined amount of G light and the exact amount of the first threshold may be altered as desired. If the determination of step S11 is YES (i.e., the amount of G light received by the light receiving element 26 is less than or equal to the first threshold TH1), the controller 50 increments the G light non-detection counter by one from the initial value of zero, and it is stored according to the current time in regards to the count value (Step S12). If the amount of G light is below the first threshold TH1, this means that the amount of light being reflected off of the tooth surface is low. This is likely due to dentifrice or some other substance in the mouth blocking the B light from reaching and being reflected off of the tooth surface. However, because the G light may be blocked for only a very brief period of time due to the dentifrice constantly moving within the user's mouth, it is not immediately necessary to clear the path to the tooth surface. Thus, the process continues from Step 12 to Step 13, described below.

After step S12, the controller 50 obtains the elapsed time (i.e., the duration of time that the G light is detected as being equal to or less than the first threshold) that is the difference between the time stored according to the latest count value of the G light non-detection counter, and the time stored according to the count value "1" of the G light non-detection counter, and determines whether or not the elapsed time is greater than or equal to a second threshold TH2 (Step S13). Thus, the second threshold is a threshold period of time, and it may be pre-determined and pre-set in the controller 50. A user may have the ability to change the value of the second threshold in some embodiments. If the amount of G light is less than or equal to the first threshold TH1 at step S11 and if the time elapsed is greater than or equal to the second threshold TH2, it may be determined that insufficient G light is being received for a sufficient period of time that the path from the light emitting element 24 to the tooth should be cleared. Specifically, at this time it may be determined that there is a substance (such as toothpaste) blocking the light from reaching and being reflected off of the teeth, which may ultimately affect the ability of the controller 50, in combination with the light receiving elements 25, 26, to determine the amount of tooth stain. Thus, at this point it may be necessary to spray fluid into the mouth to clear the path from the light emitting element 24 to the tooth surface and back to the light receiving element 26.

When the determination of step S13 is YES (the amount of G light is less than or equal to the first threshold TH1 for a period of time that is equal to or greater than the second threshold TH2), the controller 50 may operate the valve 28 and the pump 29 to supply water from the tank 30 to the fluid conduit 27 at a first supply amount and first pressure (first condition). The controller 50 may then continue to operate the fluid spray control unit to spray the liquid from the tip end of the fluid conduit 27 through the hole 21 and into the user's mouth to clear the dentifrice or other substance away so that it is not interfering with the ability of the device to sense stain amounts on the teeth (Step S14).

With the determination of step S13 being YES, it can be assumed to be in a state in which a substance (toothpaste and the like) is adhered to the tooth that blocks light. Thus, by carrying out the process of step S14, the substance adhered to the tooth can be removed, due to the liquid sprayed from the brush unit 20.

After step S14, the controller 50 resets the G light non-detection counter (returns the counter value to the initial value of zero), and clears the time stored according to the count value of the G light non-detection counter (Step S15). After step S15, the process returns to step S10, and the B light is emitted again at a predetermined timing.

When the determination of step S11 is NO, this means that the amount of G light received by the light receiving element 26 is greater than the first threshold TH1. This then means that a sufficient amount of the B light emitted from the light emitting element 24 is contacting the tooth surface and being reflected as the G light. Thus, when the determination at step S11 is NO, the controller 50 resets the G light non-detection counter, and clears the time stored according to the count value of the G light non-detection counter (Step S16). This is done because at this point spraying of liquid is not needed to obtain accurate stain sensing because a clear path to the tooth already exists. Next, the controller 50 determines whether or not the amount of light of R light received by of the light receiving element 25 is less than or equal to a third threshold value TH3 (Step S17). In this embodiment, only when the determination of Step S11 or Step S13 is NO does the controller 50 carry out the process of Step S17. Thus, Step S17 (a determination of the amount of R light being received by the light receiving element 25) only takes place when the amount of G light is greater than the first threshold or when the G light is not less than or equal to the first threshold TH1 for a time period greater than the second threshold TH2.

When the determination of step S17 is YES, this means that the amount of R light received is less than a preset threshold value TH3 such that a limited amount of R light is being detected. At this point, the controller 50 increments the R light non-detection counter by one from the initial value of zero, and it is stored according to the current time in regards to the count value (Step S18).

After Step S18, the controller 50 obtains the elapsed time (same meaning as the duration of state that R light is not detected) that is the difference between the time stored according to the latest count value of the R light non-detection counter, and the time stored according to the count value "1" of the R light non-detection counter, and determines whether or not the elapsed time is not less than the fourth threshold TH4 (Step S19). Specifically, this elapsed time is the amount of time that the R light being detected/received by the light receiving element 25 is less than or equal to the third threshold TH3.

When the determination of step S19 is YES (the amount of R light is less than the third threshold TH3 for a period of time greater than or equal to the fourth threshold TH4), the controller 50 controls the valve 28 and the pump 29, supplies water from the tank 30 to the fluid conduit 27 at a second supply amount and a second pressure (second condition), and sprays the liquid from the tip end of the fluid conduit 27 (Step S20) through the hole 21 to the user's teeth oral cavity. In certain embodiments, the first supply amount and the first pressure may be the same as the second supply amount and the second pressure, and thus the first and second conditions may be identical. In other embodiments the first and second pressures may be different while the first and second supply amounts are the same, the first and second supply amounts may be different while the first and second pressures are the same, or both the first and second supply amounts and the first and second pressures may be different.

With the determination of step S19 being YES, it is assumed to be in a state of either: (1) a first state in which the tooth is not hidden by toothpaste and the like and there are almost no stain on the teeth; (2) a second state in which the surface of the tooth is slightly visible but there is a substance such as toothpaste adhered to the tooth or in the path that blocks the light in the portion where plaque and tartar are adhering; and (3) a third state in which the light receiving element 25 is covered by toothpaste and the like. Thus, it is not automatically known the exact reason that the amount of R light is less than or equal to the third threshold TH3 for a period of time equal to or greater than the fourth threshold TH4. However, the exact reason is not important in all embodiments.

In the first state, it is possible to exhibit the function of stain sensing on tooth because nothing is blocking the tooth. However, it is not known if the low R light value is due to lack of stain on the tooth or due to the tooth being blocked. In the second state and third state, it is not possible to exhibit a function of stain sensing of the tooth because the tooth or a path from the light emitting element 24 to portions of the tooth with plaque thereon and back to the light receiving element 25 is blocked. Thus, when the determination of step S19 is YES, by the process of step S20 being carried out (spraying fluid into the mouth), the substance (i.e., toothpaste or the like) adhering to the tooth is removed, and when there is plaque or tartar, the plaque or tartar can be exposed.

In addition, by removing the substance adhering to the tooth, detection of the R light can be satisfactorily carried out.

After step S20, the controller 50 resets the R light non-detection counter (returns the counter value to the initial value of zero), and clears the time stored according to the count value of the R light non-detection counter (Step S21). After step S21, the process returns to step S10, and the B light is emitted again at a predetermined timing.

When the determination of step S17 is NO, meaning that the amount of R light being detected is greater than the third threshold (i.e., there is a lot of plaque detected on the tooth), the controller 50 resets the R light non-detection counter (returns the counter value to the initial value of zero), and clears the time stored according to the count value of the R light non-detection counter (Step S22). After that, the controller 50 calculates the amount of stain on the tooth based on the detection signal of the light receiving element 25, and the amount of stain calculated is notified from the notification unit 60 (Step S23).

After step S23, the controller 50 controls the valve 28 and pump 29 and supplies water to the fluid conduit 27 from the tank 30 at a third supply amount and a third pressure (third condition), and sprays the liquid from the tip end of the fluid conduit 27 (Step S24) through the hole 21 and into the user's mouth. After step S24, the process returns to step S10, and the B light is emitted again at a predetermined timing. In certain embodiments, the third supply amount may be lower than the first and/or second supply amounts and the third pressure may be lower than the first and/or second pressures. However, the invention is not to be so limited in all embodiments and the third supply amount and/or the third pressure may be the same or greater than the first/second supply amounts and/or the first/second pressures. Thus, variations in the exact supply amounts during the various first, second, and third conditions are possible and fall within the scope of the disclosure set forth herein.

As described above, in the electric toothbrush 100, when the timing of the determining of step S13 becomes YES, that is, when the state in which the amount of light of G light detected by the light receiving element 26 is not more than the threshold TH1 for a time period that is not less than the threshold TH2, the liquid is sprayed from the hole 21 under the first condition. Thus, even in a state in which a tooth where the plurality of tooth cleaning elements 22 are applied is covered by a substance such as toothpaste, it is possible to remove the substance by the force of the liquid. Therefore, it is possible to expose plaque and tartar adhering to the tooth, and it is possible to carry out sensing of the stain amount of the tooth.

In addition, in the electric toothbrush 100, when the timing of the determining of step S19 becomes YES, that is, when the state in which the amount of light of R light detected by the light receiving element 25 is not more than the threshold TH3 for a time period that is not less than the threshold TH4, the liquid is sprayed from the hole 21 under the second condition.

Thus, even in a state in which plaque and tartar is covered by a substance such as toothpaste, it is possible to remove the substance by the force of the liquid. Therefore, it is possible to expose plaque and tartar adhering to the tooth, and it is possible to carry out sensing of the stain amount of the tooth. In addition, even in a state in which the light receiving element 25 is covered by a substance, it is possible to remove the substance by the liquid sprayed from the hole 21, and it is possible to carry out sensing of the stain of the tooth. Thus, in certain embodiments the spray of liquid at steps S14 and S20 is for clearing a path from the light emitting element 24 to the tooth and then from the tooth back to the light receiving element(s) 25, 26. Thus, the first and second spray conditions may be configured to ensure that the spray clears the path as disclosed herein.

In addition, in the electric toothbrush 100, when the amount of light of R light exceeds threshold TH3, since the liquid is sprayed from the hole 21 at step S24, it is possible to remove the plaque by the force of the liquid, and by combing with brushing by the tooth cleaning elements 22, it is possible to increase the plaque removal effect. Thus, in some embodiments the spray of liquid at Step S24 is for plaque and tartar removal. Thus, the third spray condition may be configured to remove plaque and tartar from teeth (rather than clearing a path as with the spray of liquid at steps S14 and S20). Thus, different purposes for the liquid spray at Step 24 than at Steps 14 and 20 may require different spray conditions (pressure, spray velocity, amount of liquid, etc.).

In addition, when the determination of the step S17 is NO, there are cases when the amount of light of the G light is not more than the threshold TH1, or the tooth may be hidden by toothpaste and the like or the toothpaste and the like may be adhered to the light receiving element 26. It is possible to remove toothpaste and the like that is adhered to the tooth by the process of step S24, and it becomes easier to do better stain sensing. Thus, the spray at step S24 may be used as a fallback spray step to ensure proper stain sensing in some embodiments.

Note that, the relationship between the threshold TH2 and the threshold TH4 described in FIG. 4, is preferable such that threshold TH2<threshold TH4. The state in which the amount of light of R light is not more than the threshold TH3, includes a state in which there is no more plaque as a result of brushing. Thus, when a state continues for a short time in which the amount of light of R light is not more than the threshold TH3, the spraying of the liquid is carried out, and in a state in which there is almost no plaque adhering to the tooth and a state in which the plaque has been sufficiently reduced by the progression of brushing, the spray of the liquid is frequently carried out. Thus, in regards to threshold TH4, it is preferable to keep the value larger than threshold TH2. This will prevent a frequent spray even when the lower R light value is due to there being low amounts of plaque on the teeth as opposed to it being due to the absence of a path for the light to travel from the light emitting element 24 to the tooth and back to the light receiving element 25.

On the other hand, the state in which the amount of light of G light is not more than the threshold TH1, includes a state in which toothpaste and the like adheres to the brushing portions. In fact, a low amount of G light almost always means that there is something blocking the line of sight to the tooth. Thus, when this state is left alone for a long time, the sensing of plaque also becomes impossible because it is almost a guarantee that something is blocking the line of sight to the tooth. Therefore, concerning threshold TH2, it is preferable to keep the value smaller than threshold TH4.

As set forth above, in certain embodiments the purpose of the liquid in step S14 and step S20 may be to remove the substance blocking the light adhering to the tooth or light receiving element. On the other hand, the purpose of the liquid spray in step S24 may be to remove the plaque adhering to the tooth. Thus, since the liquid spray in step S14 and step S20 and the liquid spray in step S24 have different purposes, the spray conditions of the liquid in the respective liquid sprays may be different as described above, but the liquid spray of both may also be carried out by the same conditions.

In order to remove the toothpaste and the like, since a certain amount of liquid and pressure is necessary, as described by FIG. 4, the liquid spray in step S14 and step S20 and the liquid spray in step S24 may set different conditions. However, the removal of the toothpaste and the like is an operation not directly related to the brushing. Thus, in step S14 and step S20, the liquid spray may be carried out with a larger liquid amount and higher pressure than that of step S24. However, this may result in an uncomfortable feeling to the user. In order to reduce this uncomfortable feeling, in FIG. 4, the liquid spray in step S14 and step S20 may be carried out according to a condition with a higher supply amount or pressure than the liquid spray in step S24. As noted above, the third condition may be a condition that only reduces the supply amount of liquid relative to the first and/or second conditions, or, may be a condition that only lowers the pressure in relative to the first and/or second conditions. The terms first, second, and third preceding the term condition are merely intended to distinguish between the conditions without requiring that the conditions be different. Thus, the first, second, and/or third conditions may be the same or different in different embodiments.

In the process of step S24, since a stain of the tooth in step S23 is sensed (step S17 is no, meaning that the amount of R light, which is light that reflects off of plaque or tartar on the tooth, is greater than the third threshold TH3), the spray conditions of the liquid may be determined according to the degree of stain sensed. For example, the larger the stain, the larger the supply amount of the liquid and the higher the pressure of the liquid. Thus, the controller 50 may determine the exact amount of the stain based on the amount of the R light received by the light receiving element 25, and alter the spray condition (amount and pressure) accordingly. Thus, the amount of stain can be reduced efficiently.

In addition, since the removal of plaque itself is carried out by the oscillation of the plurality of tooth cleaning elements 22, the process of step S24 of FIG. 4 may be omitted in some embodiments. Thus, in some embodiments the spray of liquid may only be used to clear away the dentifrice or other substance so that the light can pass from the light emitting element 24 to the tooth and from the tooth to the light receiving elements 25, 26, but not also for plaque and tartar removal.

In each of the processes of step S14, step S20, and step S24 illustrated in FIG. 4, the liquid is sprayed from the hole 21. In the exemplified embodiment, the spray direction of the liquid is substantially the same as the pressing direction (first direction) in regards to the tooth of the brush unit 20 (i.e., perpendicular to the front surface 41 of the brush unit 20). Therefore, when the liquid is sprayed from the hole 21, if the brush unit 20 oscillates in the second direction, the spray path could be blocked by the tooth cleaning elements 22 due to the incline of the tooth cleaning elements 22. Specifically, when the brush unit 20 oscillates in the second direction (back-and-forth in a direction of either the opposing side edges of the brush unit 20 or the distal and proximal ends 20 of the brush unit 20), the tooth cleaning elements 22 may bend naturally due to the speed of oscillation and the flexibility/flimsiness of the tooth cleaning elements 22. As a result, in certain embodiments there may be a loss of pressure of the liquid sprayed due to the liquid contacting the bent tooth cleaning elements 22 before entering into the user's mouth. Thus, it is possible that this may weaken the effect of the removal of toothpaste and the like, or the removal of plaque. This same concern does not arise when the brush unit 20 oscillates in the first direction or mode because the tooth cleaning elements 22 do not bend in a manner that would block the fluid spray in this movement direction.

Therefore, in such embodiments the controller 50 may carry out only the first drive when carrying out each of the processes of step S14, step S20, and step S24. Specifically, the controller 50 may only oscillate the brush unit 20 in the first direction (perpendicular to the shaft of the motor and in the pressing direction of the tooth cleaning elements 22) when the controller 50 is causing the liquid to be sprayed. By doing so, when the liquid is sprayed from the hole 21, the possibility of the spray path of the liquid being blocked by the tooth cleaning elements 22 can be reduced. Thus, the possibility of weakening the effect of the removal of toothpaste and the like and the removal of plaque is reduced. In various embodiments, when other than each of the processes of step S14, step S20, and step S24 (i.e., when the fluid is not being sprayed), the controller 50 may carries out only the first drive, only the second drive, or a combination of the first drive and the second drive (alternating or the like).

In some embodiments, the controller 50, enabled to detect the brush pressure, may carry out the second drive when the brush pressure is high and may carry out the first drive when the brush pressure is low. In addition, the controller 50, enabled to detect the posture (orientation or location in the mouth) of the electric toothbrush 100, may select whether to carry out only the first drive, carry out only the second drive, or combine the first drive and the second drive, according to the detected posture.

In addition, in FIGS. 1 to 3 it is made possible to oscillate the brush unit 20 in the first direction and the second direction due to the eccentric shaft 13 and the weight 14. However, the invention is not to be so limited and the stem 11 and brush unit 20 may be in any configuration that can integrally oscillate in the first direction and the second direction. For example, the brush unit 20 may be one that can oscillate in the first direction and the second direction via sound wave oscillating. Thus, the eccentric shaft 13 and the weight 14 is just one example of a technique for oscillating the brush unit 20, and other techniques are possible and fall within the scope of the present invention.

In addition, the electric toothbrush 100 may be a simple configuration that can only oscillate the brush unit 20 mounted on the stem 11 in one direction. In addition, the electric toothbrush 100 may have a rotatable configuration of the brush unit 20 in regards to the housing of the brush unit 20 portion wherein the plurality of tooth cleaning elements 22 are provided, and may be a configuration such that the brush unit 20 is driven by the drive mechanism provided in the stem 11 which rotates this portion and carries out a tooth brushing operation.

Figure 5:
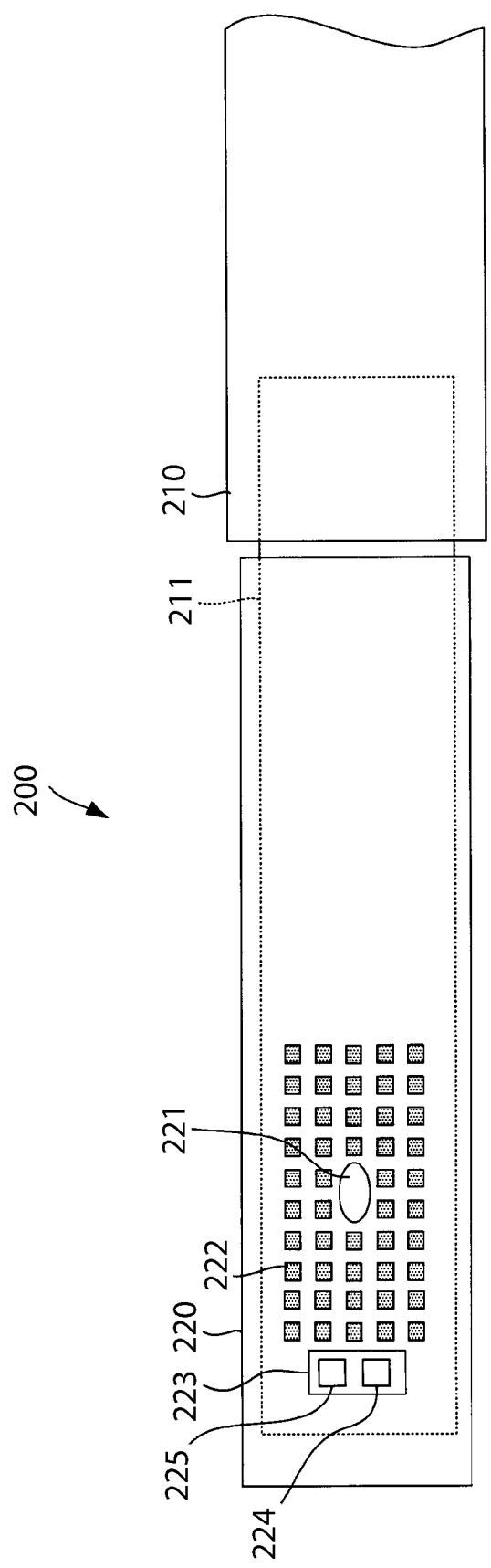
FIG. 5 is a top view of an electric toothbrush in accordance with a second embodiment of the present invention.

FIG. 5 is a planar view illustrating a schematic configuration in which the electric toothbrush 200 that is a modification of the electric toothbrush 100 illustrated in FIG. 1, is viewed from the brush pressing direction. The electric toothbrush 200 is similar to the electric toothbrush 100 except as described herein. The electric toothbrush 200 is similarly numbered to the electric toothbrush 100 except that the 200-series of numbers is used. Thus, for components of the electric toothbrush 200 that are similarly numbered to components of the electric toothbrush 100, it should be appreciated that the description of that component above with reference to the electric toothbrush 100 is applicable.

The electric toothbrush 200 is the same configuration as the electric toothbrush 100, except that the light receiving element 26 is removed. Thus, the electric toothbrush 200 includes a light emitting element 224 and a light receiving element 225 that receives R light, but not also a light receiving element that includes G light. All other features of the electric toothbrush 200 are identical to the electric toothbrush 100 and thus the description above is applicable. The electric toothbrush 200 is capable of function similar to the electric toothbrush 100 despite the omission of the light receiving element receiving G light.

Figure 6:
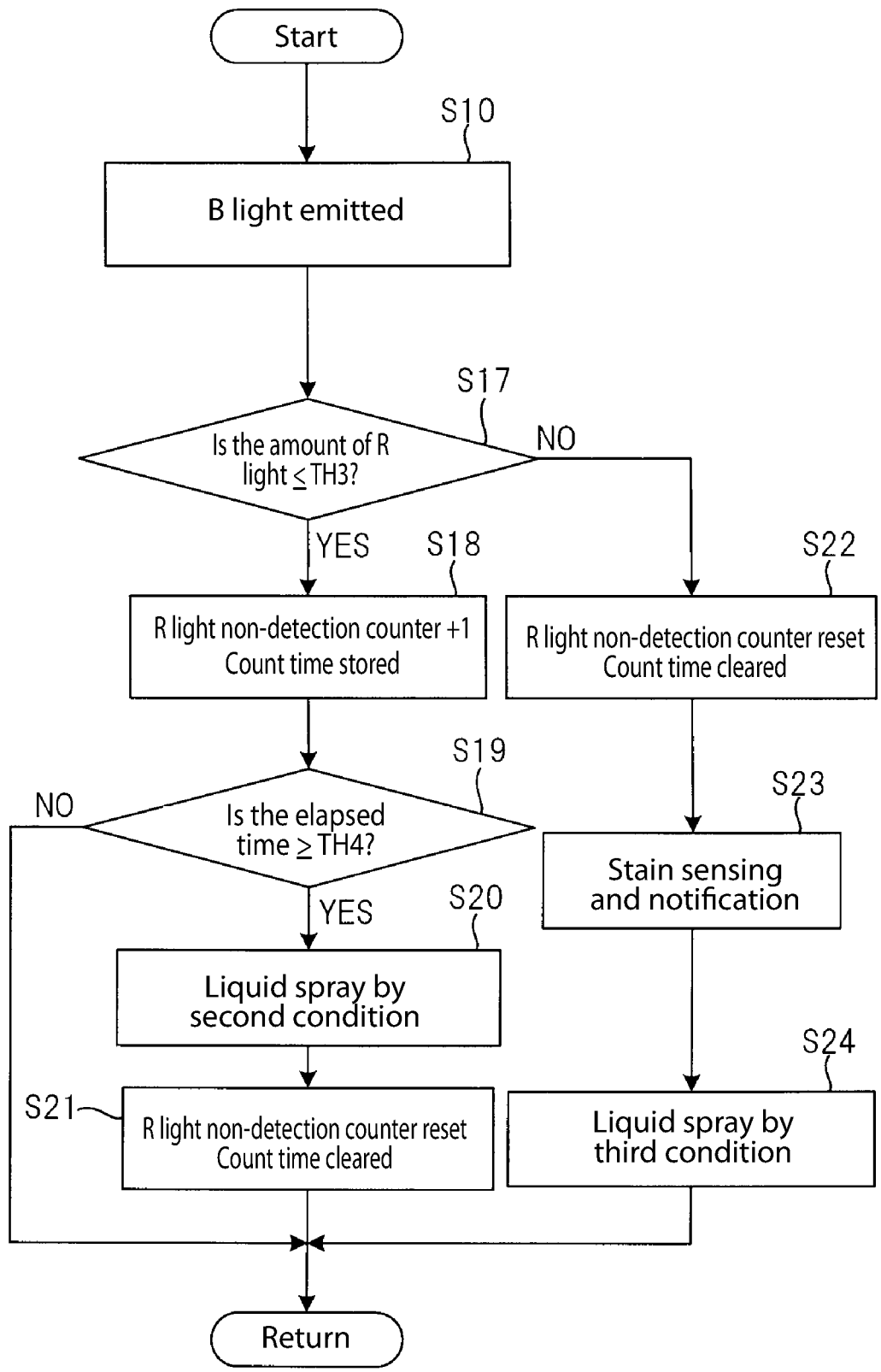
FIG. 6 is a flowchart for describing an operation of the electric toothbrush of FIG. 5.

FIG. 6 is a flowchart for describing an operation of the electric toothbrush 200 illustrated in FIG. 5. In FIG. 6, the same steps described in FIG. 4 are denoted by the same reference numerals and that description of FIG. 4 above may be referred to for clarity as to what is shown in FIG. 6. The controller (not shown with regard to this embodiment, but the controller 50 described above is applicable) of the electric toothbrush 200 carries out the steps of step S17 and subsequent steps described in FIG. 4, after emitting the B light in step S10. Basically, in this embodiment steps S11 through S16 from the previous embodiment are omitted because they relate to the receiving of G light, which does not occur in this embodiment. However, step S10 and S17 through S24 do occur in an identical manner to the previous embodiment. In the interest of brevity, these steps will not be described again here, it being understood that the description above with reference to FIG. 4 is applicable.

As described above, even in a configuration without the light receiving element that receives G light, by the liquid being sprayed from the hole 221 when a state in which the amount of light of R light detected by the light receiving element 25 is not more than the threshold TH3 for a time period that is not less than threshold TH4, it is possible to reduce the state in which sensing of the stain amount of the tooth cannot be carried out. Specifically, the liquid spray at step S20 will still clear the path for the light to be emitted onto the tooth and reflected back to the light receiving element 25.

Note that in the electric toothbrush 100 of FIG. 1, regardless of the amount of light of R light, the liquid is sprayed from the hole 21 when the state in which the amount of light of G light is not more than the threshold TH1 for a time period that is not less than the threshold TH2. Thus, in the previously described embodiment of the electric toothbrush 100, not only is the R light, but the amount of light of G light is also monitored, and controlling the spray timing of the liquid is based on the size of the amount of G light and/or the amount of R light.

Figure 7:
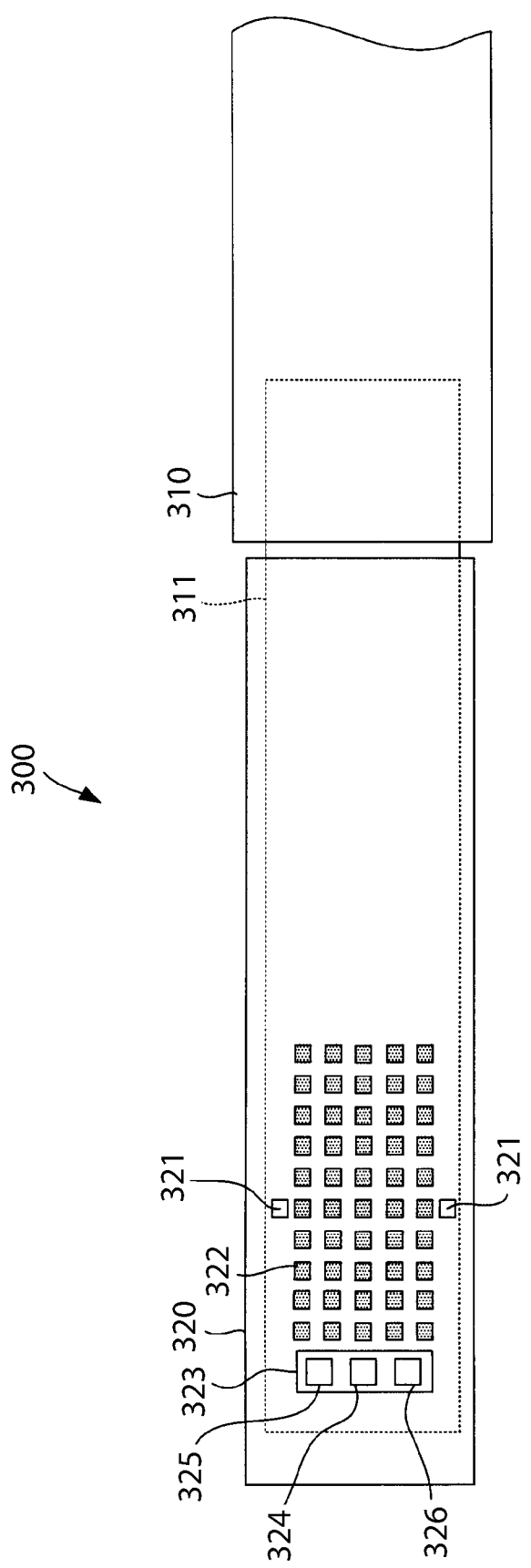
FIG. 7 is a top view of an electric toothbrush in accordance with a third embodiment of the present invention.

FIG. 7 is a planar view illustrating a schematic configuration in which the electric toothbrush 300 that is a modification of the electric toothbrush 100 illustrated in FIG. 1, is viewed from the brush pressing direction. The electric toothbrush 300 is similar to the electric toothbrush 100 except as described herein. The electric toothbrush 300 is similarly numbered to the electric toothbrush 100 except that the 300-series of numbers is used. Thus, for components of the electric toothbrush 300 that are similarly numbered to components of the electric toothbrush 100, it should be appreciated that the description of that component above with reference to the electric toothbrush 100 is applicable.

The electric toothbrush 300 is the same configuration as the electric toothbrush 100, except that the position of the hole 321 through which the liquid is sprayed is different. Specifically, in this embodiment two holes 321 are provided in the brush unit 320 of the electric toothbrush 300. The two holes 321 are disposed to be across from each other in a region formed by the plurality of brushes 322. Stated another way, rather than being located within the field of tooth cleaning elements 322 and surrounded by the tooth cleaning elements 322, the two holes 321 are positioned closer to the lateral sides of the brush unit 320 than the outermost ones of the tooth cleaning elements 322. According to this configuration, the number of tooth cleaning elements 322 can be increased compared to the electric toothbrush 100 because the holes 321 are external to the field of the tooth cleaning elements 322 rather than being centrally located within the field of the tooth cleaning elements 322.

In the electric toothbrushes 100 and 300, a light receiving element 25, 325 is used as a reflected light detecting module for detecting the R light that is the reflected light of the B light, and a light receiving element 26, 326 is used as a reflected light detecting module for detecting the G light that is the reflected light of the B light. Instead of the light receiving element 25, 325 and the light receiving element 26, 326, an imaging element disposed in a two-dimensional shape (for example, a staggered shape) with a photoelectric conversion element for detecting R light, and a photoelectric conversion element for detecting G light, may be used as the reflected light detecting module for detecting the reflected light of the B light.

When using an imaging device, among the output signals of the photo electric conversion element group for detecting R light (G light), the total number of output signals that has a minimum detection signal or above, may be treated as the amount of light of R light (G light). In addition, among the output signals of the photo electric conversion element group for detecting R light (G light), the cumulative value of output signals that has a minimum detection signal or above, may be treated as the amount of light of R light (G light).

Figure 8:
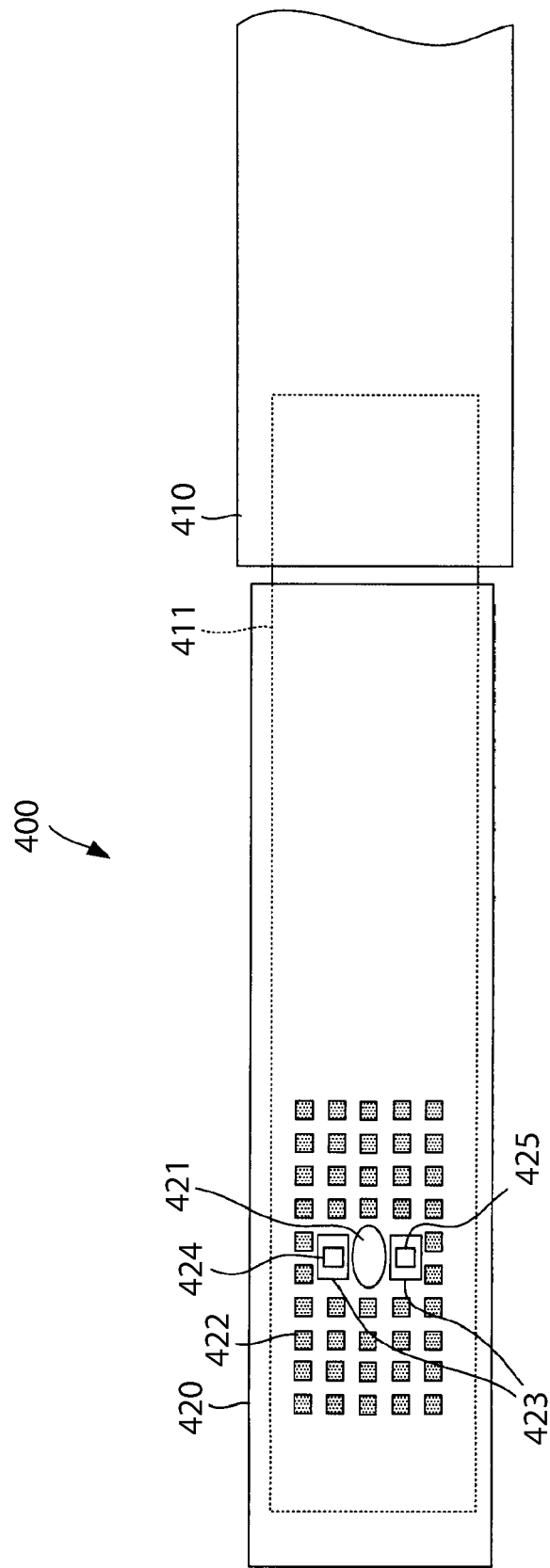
FIG. 8 is a top view of an electric toothbrush in accordance with a fourth embodiment of the present invention.

FIG. 8 is a planar view illustrating a schematic configuration in which the electric toothbrush 400 that is a modification of the electric toothbrush 200 illustrated in FIG. 5, is viewed from the brush pressing direction. The electric toothbrush 400 is similar to the electric toothbrush 200 except as described herein. The electric toothbrush 400 is similarly numbered to the electric toothbrush 200 except that the 400-series of numbers is used. For components of the electric toothbrush 400 that are similarly numbered to components of the electric toothbrush 100, it should be appreciated that the description of that component above with reference to the electric toothbrush 100 is applicable.

The electric toothbrush 400 is the same configuration as the electric toothbrush 200, except with respect to the positioning of the light emitting element 424 and the light receiving element 425 in the stem 411. Furthermore, the position of the transparent window 423 formed in the housing of the brush unit 420 in regards to the light emitting element 424 and the light receiving element 425 is different.

The light emitting element 424 and the light receiving element 425 built into the stem 411 of the electric toothbrush 400, as viewed from the brush pressing direction, are disposed so as to be on either side of the hole 421. Then, the transparent window 423 is formed in the housing of the brush unit 420 opposing the light emitting element 424 and the light receiving element 425

The operation of the electric toothbrush 400 is the same as the electric toothbrush 200. According to the electric toothbrush 400, since the transparent window 423 opposite of the light receiving element 425 and the light emitting element 424 is close to the hole 421, the substance adhering to the transparent window 423 can be effectively removed by the liquid sprayed from the hole 421.

In the electric toothbrushes 100 to 400, a light emitting element and a light receiving element included in the light detecting part, is provided in the stem 11, 211, 311, but the light emitting module and the reflected light detecting module may be provided on the outside surface of the housing (the same surface formed by the tooth cleaning elements 22, 622, 322, 422) of the brush unit 20, 220 320, 420. In this case, the light emitting element functions as the light emitting module. According to the electric toothbrushes 100 to 400, it is possible to suppress the manufacturing cost of the consumable brush unit 20, 220 320, 420 as much as possible.

In the embodiments described above, the configuration for spraying a liquid from the hole 21, 221, 321, 421 has been described, but it may be configured to spray a gas such as air from the hole 21, 221, 321, 421 instead of a liquid. Thus, in certain embodiments the material being sprayed is referred to herein as a fluid, which includes a liquid and a gas. In certain embodiments, in the electric toothbrushes 100 to 400, if there is no liquid in the tank 30, air can be sprayed from the hole 21, 221, 321, 421. Thus, the electric toothbrush 100 to 400 may be configured so that a fluid including a liquid or a gas can be sprayed from the hole 21, 221, 321, 421. In some embodiments, the electric toothbrushes 100 to 400 may be configured to spray only a liquid or only a gas, and in other embodiments the electric toothbrushes 100 to 400 may be configured to spray either a liquid or a gas depending on what is in the tank 30. In certain embodiments, using a liquid as the fluid is preferred as it is more effective at plaque removal and the removal of toothpaste as described herein.

Figure 9:
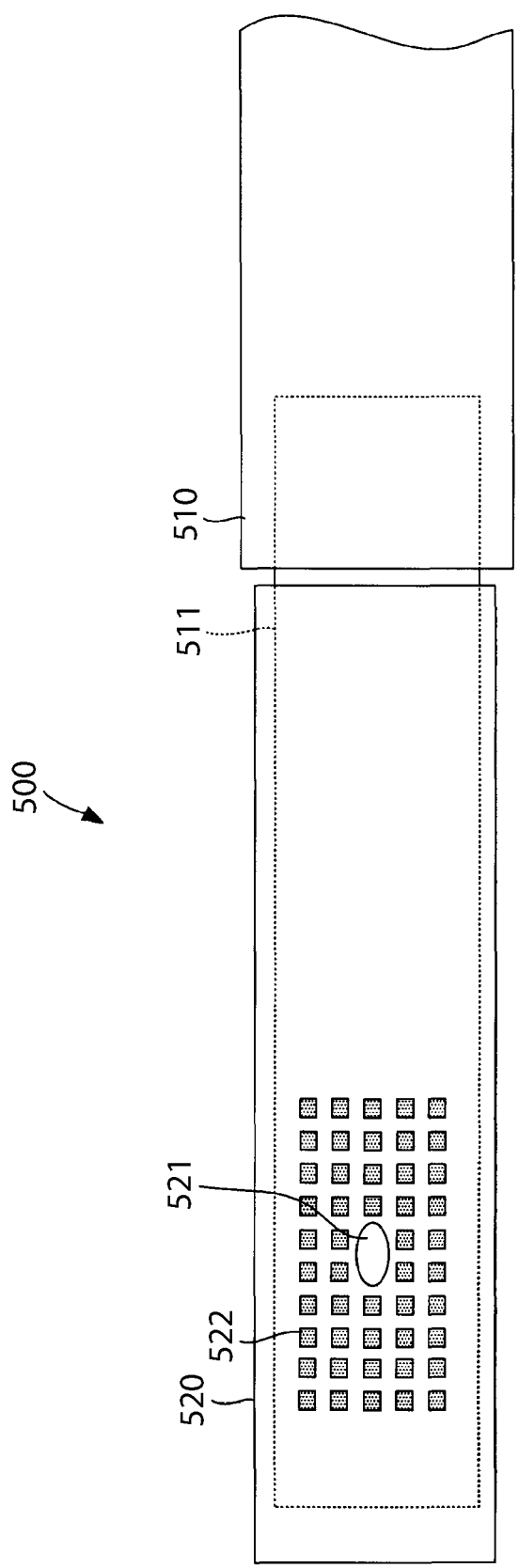
FIG. 9 is a top view an electric toothbrush in accordance with a fifth embodiment of the present invention.

FIG. 9 is a plan view illustrating a schematic configuration seen from the brush pressing direction of an electric toothbrush 500 that is a modified example of the electric toothbrush 100 illustrated in FIG. 1. The electric toothbrush 500 is similar to the electric toothbrush 100 except as described herein. The electric toothbrush 500 is similarly numbered to the electric toothbrush 100 except that the 500-series of numbers is used. Thus, for components of the electric toothbrush 500 that are similarly numbered to components of the electric toothbrush 100, it should be appreciated that the description of that component above with reference to the electric toothbrush 100 is applicable.

The electric toothbrush 500 is the same configuration as the electric toothbrush 100 except that the transparent window 23, the transparent window 23a, the light emitting element 24, the light receiving element 25, the light receiving element 26, and the substrate 15 are removed from the device. Thus, the electric toothbrush 500 includes a hole 521 and the other components necessary for spraying a fluid through the hole 521, but the light emitting and light receiving elements 24, 25, 26 and associated other components are omitted. In the electric toothbrush 500, spraying of a fluid from the hole 521 is performed for the removal of plaque, food remains, or the like in the mouth. The controller of the electric toothbrush 500 controls the valve and the pump at a predetermined timing, or a timing indicated by the user of the electric toothbrush 500, and performs a control spraying a fluid from the hole 21. The controller of the electric toothbrush 500 controls the motor M in the same way as the controller 50 of the electric toothbrush 100 and drives the brush unit 20. It is noted that the controller, valve, pump, tank, and fluid conduit are not specifically shown in FIG. 9, but the details of those components are illustrated in FIGS. 2 and 3 and described above are applicable.

When the power of the electric toothbrush 500 is on and the brushing manipulation starts, the controller of the electric toothbrush 500 starts the control alternately performing the first driving and the second driving. By this, the brush unit 520 pressed to the tooth alternately repeats the oscillation in the first direction and the oscillation in the second direction, and the plaque adhering to the tooth is removed by the tooth cleaning elements 522.

The controller of the electric toothbrush 500 pauses alternately performing the first driving and the second driving at a predetermined timing, or when the fluid sprays indicated by the user of the electric toothbrush 500 after brushing starts, and performs only the first driving. Furthermore, the controller controls the valve and the pump, supplies liquid or gas from inside of the tank to the fluid conduit at a specified supply amount and a specified pressure, and sprays a fluid from the tip end of the fluid conduit.

The controller of the electric toothbrush 500 controls the motor M and restarts the control alternately performing the first driving and the second driving when the spraying of the fluid ends. Hereafter, the controller performs the same action at a predetermined timing, or at a fluid spraying indicated by the user. Thus, as described briefly above, in this embodiment the electric toothbrush 400 (or the brush unit 520 thereof) only oscillates in the first driving when the fluid is being sprayed. This is because in the second driving, the flexibility/movement of the tooth cleaning elements 522 causes the tooth cleaning elements 522 to block the fluid spray, which reduces its positive effects. By only oscillating in the first driving when fluid is being sprayed, it can be ensured that the fluid reaches its intended target because it is not blocked by the tooth cleaning elements 522.

As above, according to the electric toothbrush 500, as was described before, the pressure loss of the fluid can be made to the lowest limit and the removal effect of plaque or the like can be enhanced when the fluid is sprayed from the hole 521 since only the first driving is performed. On the other hand, plaque can be effectively removed when the fluid is not sprayed from the hole 521 since the first driving and the second driving are performed alternately.

Note that when the fluid is not sprayed from the hole 521, the controller may perform only the first driving, perform only the second driving, or the like, rather than alternating between the first driving and the second driving (or the first and second modes). For example, the brush pressure may be made able to be detected, and the controller performs only the second driving when the brush pressure is high, and performs only the first driving when the brush pressure is low. Furthermore, the posture, orientation, or location of the electric toothbrush 500 may be made able to be detected, and the controller may choose whether to perform only the first driving, perform only the second driving, or perform the first driving and the second driving in combination based on the detected posture.

Figure 10:
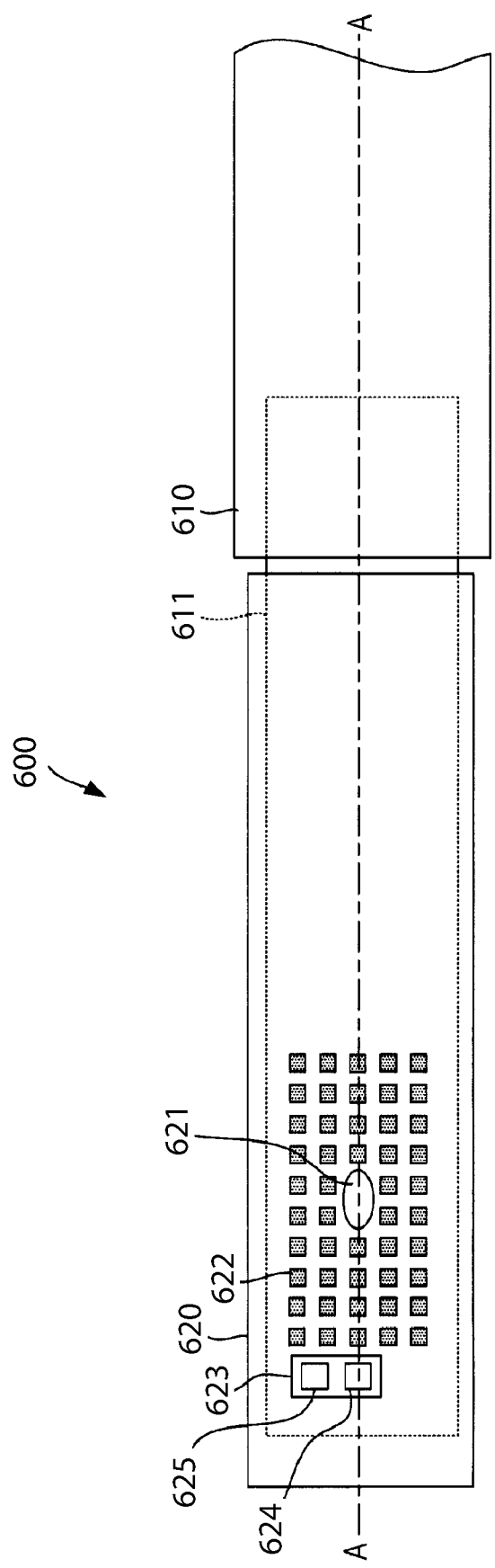
FIG. 10 is a top view an electric toothbrush in accordance with a sixth embodiment of the present invention.

FIG. 10 is a planar drawing showing a simplified configuration of an electric toothbrush 600 from the direction of pressing, for describing an embodiment of the present invention. The electric toothbrush 600 is similar to the electric toothbrush 200 in that it only includes one, rather than two, light receiving elements. Nonetheless, the full details of the electric toothbrush 600 will be provided below. The electric toothbrush 600 comprises a gripping portion 610 containing a battery and an electric control system in its interior, a main body having a stem 611 fixed to the gripping portion 610, and a brush unit 620 that can be attached to and removed from to the stem 611. For the details of the brush unit 620 and its coupling to the stem 611, the description with regard to FIGS. 1 and 2 above is applicable.

The brush unit 620 comprises a plurality of tooth cleaning elements 622 extending from the front surface thereof, a hole 621 formed into the front surface for spraying liquid, and a transparent window 623 so that light from a light emitting element 624 can pass therethrough and reflected light can pass therethrough back to a light receiving element 625. For the specific details of the tooth cleaning elements 622, the description of the tooth cleaning elements 622 above with regard to FIGS. 1 and 2 is applicable.

In this embodiment, the hole 621 is disposed in a region surrounded by the tooth cleaning elements 622 similar to the configuration of FIGS. 1 and 2, although the invention is not to be so limited and the hole 621 may be positioned at other locations along the brush unit 620. The transparent window 623 is located similarly to the location described above with regard to FIGS. 1 and 2, although it can be placed at other locations in other embodiments. The transparent window 623 is formed by fitting a translucent member such as a transparent resin or transparent glass or the like into a hole provided on the housing of the brush unit 620. The transparent window 623 is disposed closer to the distal end of the brush unit 620 than the region formed by the plurality of tooth cleaning elements 622 and it is on the surface of the brush unit 620 from which the plurality of tooth cleaning elements 622 extend (i.e., the front surface). The position of the transparent window 623 is one example, and the invention is not limited to the position shown in FIG. 10. The transparent window 623 should be disposed to allow light emission in the direction that the tooth cleaning elements 622 extends, from the plane on which the tooth cleaning elements 622 is formed.

Figure 11:
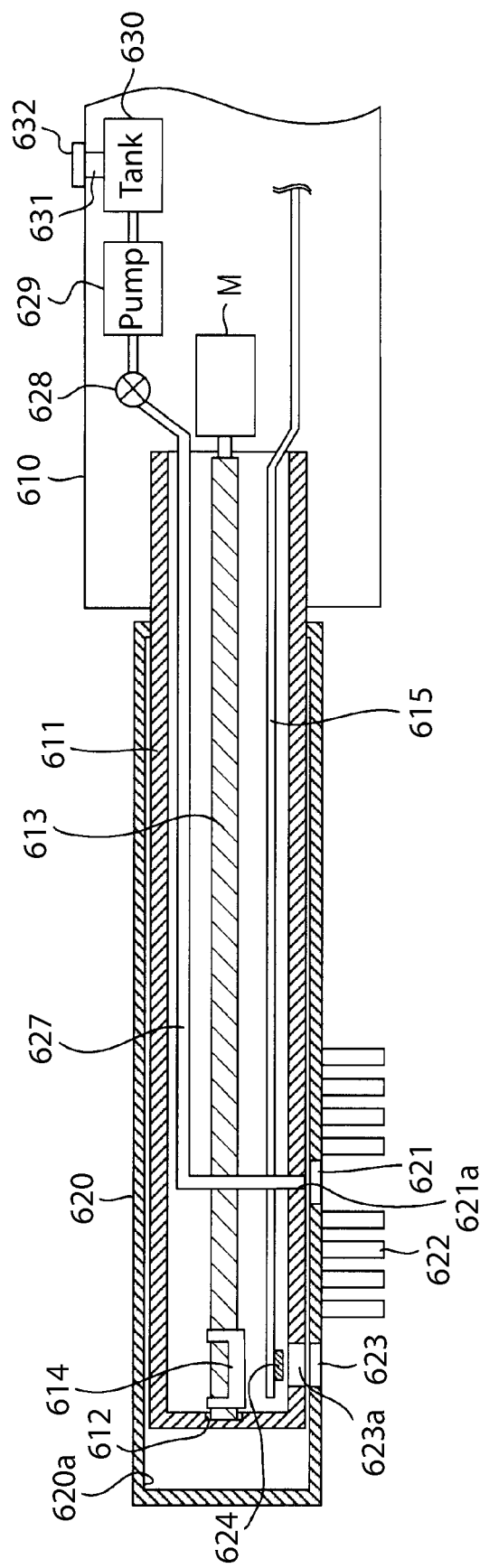
FIG. 11 is a cross-sectional view taken along line A-A of FIG. 10.

FIG. 11 is a cross-sectional pattern diagram of line A-A of the electric toothbrush 600 shown in FIG. 10. The brush unit 620 is composed of a tube-shaped housing closed on the front end part having a hollow part 620a. The brush unit 620 is installed on the main body by positioning the stem 611 within the hollow part 620a. The stem 611 is composed of a tube-shaped housing with the front end part (the end part opposite the side of the gripping portion 610) closed. The stem 611 comprises a bearing 612 formed on the front end of the interior, an eccentric shaft 613, one end of which is inserted into the bearing 612, a weight 614, a substrate 615, a light emitting element 624 formed on the substrate 615, a light receiving element 625 formed on the substrate 615 (see FIG. 10), a transparent window 623a provided on the housing, and a fluid conduit 627. The features that are numbered similarly to the features of the electric toothbrush 100 in FIGS. 1 and 2 have similar structure and function, and thus the description of those features provided above with reference to FIGS. 1 and 2 is applicable to this embodiment as well except where it conflicts with the disclosure set forth below.

The gripping portion 610 comprises a valve 628 connected to the fluid conduit 627 that extends from inside the stem 611, a pump 629 connected to the valve 628, a tank 630 connected to the pump 629, a liquid supply opening 631 for pouring liquid in the tank 630, a cap 632 for closing the liquid supply opening 631, and a motor M linked to the eccentric shaft 613 in the stem 611. The other end of the eccentric shaft 613 is linked to the rotating shaft of the motor M contained in the gripping portion 610. The eccentric shaft 613 rotates by the rotation of the rotating shaft of the motor M.

The weight 614 is fixed to the eccentric shaft 613 in the vicinity of the bearing 612. The center of gravity of the eccentric shaft 613 is offset from the center of rotation by the weight 614. Note that a minute clearance is provided between the bearing 612 and the eccentric shaft 613. The eccentric shaft 613 rotates with the rotation of the rotating shaft of the motor M, but because the center of gravity of the eccentric shaft 613 is offset by the weight 614, it performs a movement as if it gyrates around the center of rotation. Thus, the tip of the eccentric shaft 613 repeatedly collides relative to the inner wall of the bearing 612, thereby causing the stem 611 and the brush unit 620 installed thereon to oscillate at high speed. In this manner, with the drive principle of the oscillation of the brush unit 620 due to the gyration movement of the eccentric shaft 613, the brush unit 620 can oscillate two-dimensionally in a plane perpendicular to the rotating shaft of the motor M.

The electric toothbrush 600 can switch between the operation wherein the stem 611 and the brush unit 620 are oscillated in a first mode in the direction of pressing the tooth cleaning elements 622 and the operation wherein the stem 611 and the brush unit 620 are made to oscillate in a second mode in a direction intersecting (preferably perpendicular to) the direction of pressing the tooth cleaning elements 622 (which may be in a plane perpendicular to the rotating shaft of the motor M). Note that the direction of pressing the tooth cleaning elements 622 is the same as the direction that each tooth cleaning elements 622 extends. Also, the direction of pressing the tooth cleaning elements 622 is perpendicular to the direction in which the rotating shaft of the motor M extends.

As shown in FIG. 11, in the housing of the stem 611, a transparent window 623a that is substantially the same size as the transparent window 623 is formed on the portion opposing the transparent window 623 of the housing of the brush unit 620. The transparent window 623a is formed by fitting a translucent member such as a transparent resin or a transparent glass in the hole provided on the housing of the stem 611. The light emitting element 624 and the light receiving element 625 illustrated in FIG. 10 are disposed on the substrate 615 positioned opposing the transparent window 623a.

The light emitting element 624 is configured as a LED (Light-emitted diode) or laser diode or the like. As for the light emitting element 624, something that emits light in the blue wavelength region (referred to herein below as B light) necessary for detecting plaque, which is the object subject to detection, is used. The B light emitted from the light emitting element 624 passes through the transparent window 623a and the transparent window 623 and is emitted to the exterior of the brush unit 620. The light emitting element 624, the transparent window 623a, and the transparent window 623 function as the light emitting module for emitting light from the brush unit 620.

The light receiving element 625 is configured as a photoelectric conversion element, such as a photodiode or the like, for converting light into an electric signal. The light receiving element 625 is configured from a photoelectric conversion element that detects light in the red wavelength region (referred to herein below as R light) and outputs a signal according to the amount of detected light. The light receiving element 625 is configured as a combination of a color filter that transmits R light and a photodiode having sensitivity to visible light, a photodiode that can detect only R light, or the like.

When B light is emitted onto plaque adhered to a tooth, R light is excited in the plaque. That is, R light is generated as reflected light of the B light. The light receiving element 625 is provided for detecting the R light obtained from the B light emitted from the light emitting element 624 reflecting from the plaque. Thus, the light receiving element 625 functions as a reflected light detector for detecting the R light that is reflected light of the B light emitted from the light emitting module. This concept has been described in detail above with reference to FIGS. 1-4 and should be readily understood at this point.

The substrate 615 has a wire connection electrically connecting to the light emitting element 624 and the light receiving element 625, and, for example, a flexible substrate is used. The substrate 615 extends into the gripping portion 610, and the wire connections formed on the substrate 615 are electrically connected to a controller 650 contained in the gripping portion 610 that is described later.

The tank 630 holds liquid inserted via the liquid supply opening 631. The liquid may be, for example, water, a cleansing liquid having a plaque breakdown effect, mouthwash, another type of oral care agent, or the like. Although described herein as being a liquid, the material in the tank 630 may be a fluid, which can include gases such as air in other embodiments.

The pump 629 sucks up the liquid held in the tank 630 and supplies it to the valve 628. The valve 628 is coupled to the base end of the fluid conduit 627 extending from inside the stem 611, and controls the supply amount and supply pressure of the liquid supplied to the fluid conduit 627, as well as the supply timing of liquid to the fluid conduit 627.

The fluid conduit 627 is configured as a pipe-shaped member that can pass liquid therethrough. Within the housing of the stem 611, a hole 621a is provided on the portion opposing the hole 621 of the brush unit 620. The front end of the fluid conduit 627 is fitted in the hole 621a. By this configuration, the liquid sprayed from the front end of the fluid conduit 627 passes through the hole part 621 of the brush unit 620 and is sprayed to the exterior of the brush unit 620.

The pump 629, the valve 628, the fluid conduit 627, the hole 621a, and the hole 621 function as the fluid spray module for spraying fluid from the brush unit 620. The spray direction of the liquid sprayed from the brush unit 620 can be changed by changing the cross-sectional shape of the hole 621. The spray direction is preferably a direction such that the angle formed with the direction of pressing the tooth cleaning elements 622 is less than 90 degrees, and it is particularly preferable for it to be the same as the direction of pressing the tooth cleaning elements 622 (the direction that the tooth cleaning elements 622 extends).

Figure 12:
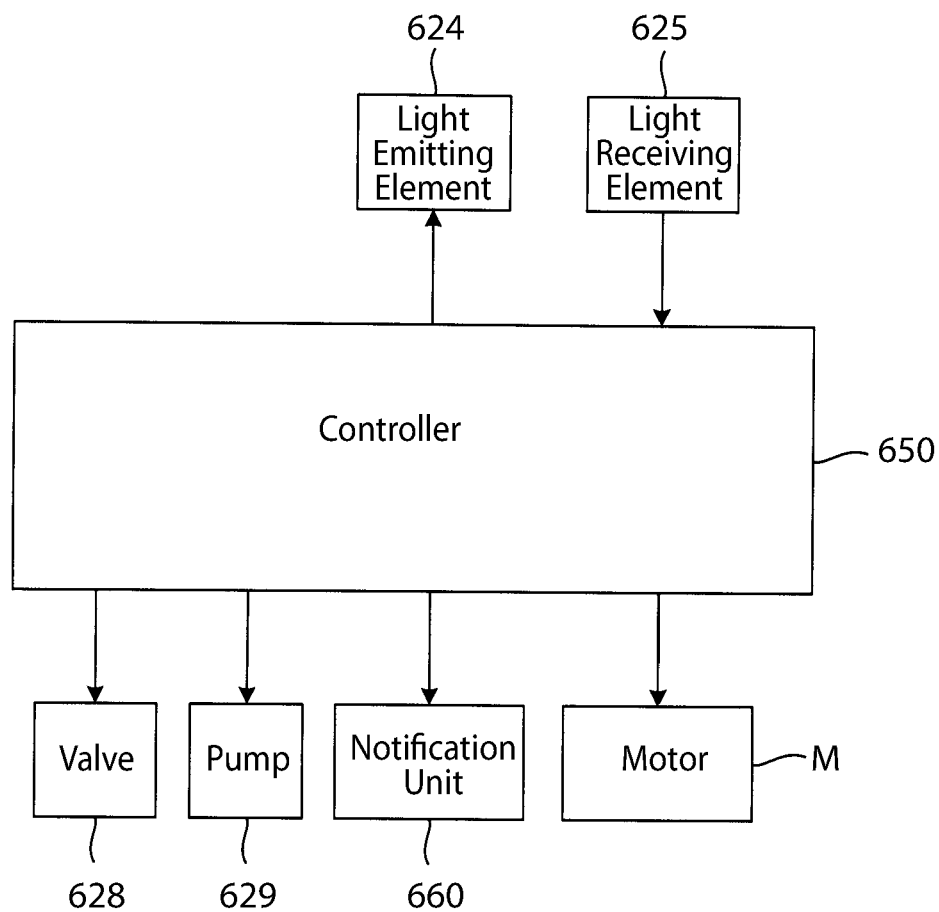
FIG. 12 is a block diagram showing the internal configuration of a main body of the electric toothbrush of FIG. 10.

FIG. 12 is a block diagram showing the internal configuration of the main body of the electric toothbrush 600 shown in FIG. 10. The main body of the electric toothbrush 600 is composed of the motor M, a notification part 660, the controller 650, the pump 629, and the valve 628. As shown in FIG. 12, each of the valve 628, the pump 629, the notification unit 660, the motor M, the light emitting element 624, and the light receiving element 625 is operably coupled to the controller 650. This enables the controller 650 to communicate with each of these components to provide instructions to or receive data from these components to achieve appropriate function and operation of the electric toothbrush 600 similar to that which has been described above with reference to FIGS. 1-4.

The controller 650 functions as a drive module selectively performing a first drive for oscillating the brush unit 620 in the direction of pressing the tooth cleaning elements 622 which is a first direction, and a second drive for oscillating the brush unit 620 in a second direction (here, the direction intersecting the direction of pressing the tooth cleaning elements 622 within the plane perpendicular to the rotating shaft of the motor M) that is different from the first direction. Note that the configuration may have the controller 650 oscillate the brush unit 620 in a second direction that is an arbitrary direction (for example, the direction in which the rotating shaft of the motor M extends) within a plane perpendicular to the first direction. Thus, while the first direction may be up-and-down (away from and towards the front surface of the brush unit 620), the second direction may be side-to-side between the opposing sides of the brush unit 620 or back-and-forth between the distal and proximal ends of the brush unit 620. In some embodiments, the invention is not to be particularly limited by the exact movement imparted by the first and second drives/modes/directions as long as they are different. In some embodiments, the controller 650 switches between the first drive and the second drive by changing the rotating speed of the rotating shaft of the motor M, although other techniques are possible to achieve this in other embodiments.

The controller 650 alternatingly performs, for example, the first drive and the second drive. In this manner, by automatically switching the oscillation direction of the brush unit 620, because the tips of the hairs of the tooth cleaning elements 622 are applied to the area to be treated from a variety of angles, a superior plaque removal effect can be obtained compared to unidirectional brushing.

The controller 650 drives the light emitting element 624 via the substrate 615, and performs control of B light emission from the light emitting element 624. Furthermore, the controller 650 performs a plaque/tartar/stain detection process for detecting plaque/tartar/stain adhered to the teeth based on the reflected light detected by the light receiving element 625. The plaque detection process is performed by the known method based on the amount of light of R light (detection signal level) detected at the light receiving element 625. In this regard, the controller 650 functions as a plaque detector.

The controller 650 controls the liquid spray timing from the hole 621 based on the plaque detection results. In this role, the controller 650 functions as a fluid spray controller.

The notification part 660 performs notification of the plaque levels to the user of the electric toothbrush 600 by using a device such as a speaker, LED, or the like. The notification part 660 follows the commands from the controller 650 and performs notification to the user by playing a sound or lighting an LED. The content of the notification is set to be the amount of plaque calculated by the controller 650. For example, the notification part 660 may light the LED a green color when in a state of having a very small amount of plaque, and light the LED a red color when in a state of having a large amount of plaque or the like to notify of the amount of plaque and support effective brushing of the teeth. Of course, these colors are merely exemplary and are not intending to be limiting in any way. In some embodiments, the LED may light up only when the plaque levels are deemed sufficiently high (i.e., higher than a threshold value) but not also when the plaque levels are low.

Figure 13:
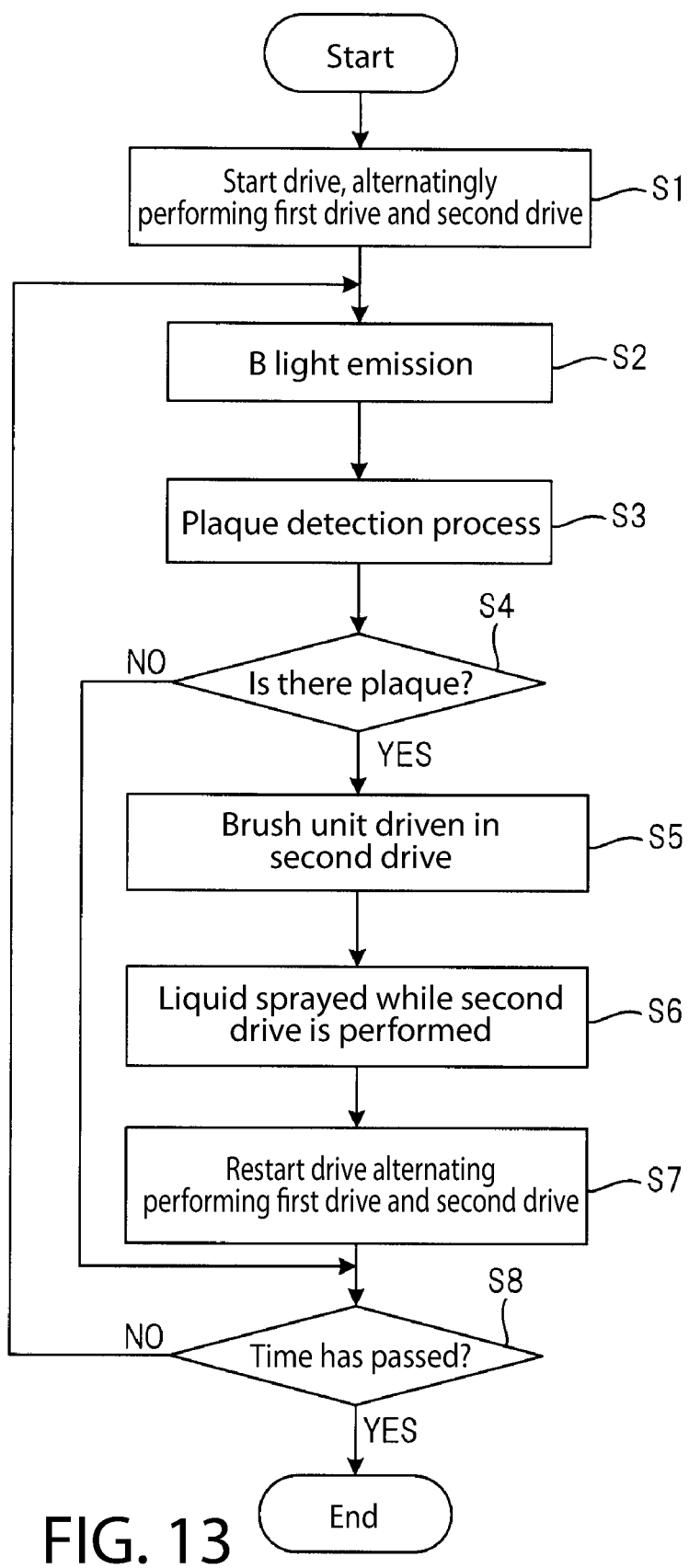
FIG. 13 is a flow chart for describing the operation of the electric toothbrush of FIG. 10.

FIG. 13 is a flow chart for describing the operation of the electric toothbrush 600 shown in FIGS. 10 and 11. When the power of the electric toothbrush 600 is turned on and the brushing start operation is performed, the controller 650 starts the drive of alternatingly performing the first drive and the second drive (step S1). This causes the brush unit 620, which is pressed against the teeth, to alternatingly repeat oscillation in the first direction and oscillation in the second direction, and plaque adhered to the teeth is removed by the tooth cleaning elements 622. The controller 650 may drive the brush unit 620 to alternate the oscillation types (first drive and second drive) based on a preset time, based on orientation of the brush unit 620 in the mouth, based on brushing pressure, or the like. Furthermore, in some embodiments the controller 650 may only drive one type of oscillation rather than two.

In some embodiments, the controller 650 causes the light emitting element 624 to emit light at a predetermined timing while alternatingly performing the first drive and the second drive. As a result, the B light emitted from the light emitting element 624 is emitted through the transparent window 623 to the exterior of the brush unit 620 (step S2). The controller 650 acquires the output signal of the light receiving element 625 immediately following light emission from the light emitting element 624. Specifically, the light receiving element 625 essentially immediately receives the reflected R light upon the B light reflecting off of plaque on the tooth, and data indicative of the amount of R light is transmitted to the controller 650 for processing. Thus, the controller 650 detects the amount of plaque adhered to the teeth (step S3) based on the amount of light of R light detected by the light receiving element 625 (the detection signal level of the light receiving element 625).

The controller 650 stops driving/oscillating the brush unit 620 the first drive and drives the brush unit 620 with only the second drive (step S5) when the amount of plaque calculated by the plaque detection process exceeds a threshold and it is determined that there is plaque (step S4: YES). The controller 650 moves process to step S8 if the amount of plaque calculated by the plaque detection process is below threshold and it is determined that there is no plaque (step S4: NO).

In step S5, with the brush unit 620 in a condition such that it is being driven in the second drive, the controller 650 controls the valve 628 and the pump 629, supplies the liquid in the tank 630 to the fluid conduit 627 at a predetermined supply amount and predetermined pressure, and sprays liquid from the front tip of the fluid conduit 627 (step S6). The liquid is preferably sprayed into the user's mouth, and more preferably onto the user's teeth, to assist in plaque removal. After the liquid is sprayed for an adequate and pre-determined period of time, the controller 650 closes the valve 628 and stops the spraying of the liquid. The pre-determined period of time may change in some embodiments based on the amount of plaque detected in step S4. When the controller 650 closes the valve 628 and finishes the spraying of the liquid, it resumes driving by alternatingly performing the first drive and the second drive (step S7).

After step S7, the controller 650 finishes the brushing operation if a predetermined amount of time has passed since the start of the brushing operation (step S8: YES). On the other hand, if a predetermined amount of time has not passed since the start of the brushing operation (step S8: NO), the controller 650 returns processes to step S2.

As described above, the electric toothbrush 600 sprays liquid from the hole 621 when the amount of plaque exceeds a threshold. Also, while this liquid is being sprayed, the brush unit 620 only oscillates in the second direction. In a state such that the plurality of the tooth cleaning elements 622 are applied to the surface of the teeth during teeth cleaning, oscillating the brush unit 620 in the second direction makes it difficult for the liquid sprayed from the hole 621 to leak outside the gaps between each tooth cleaning elements 622. Specifically, in the second direction the brush unit 620 oscillates side-to-side or back-and-forth (the details of which have been described above), which causes the tooth cleaning elements 622 to bend/flex and block the flow path of the liquid as it exits through the hole 621. Thus, by oscillating the brush unit 620 in the second direction during the liquid spraying action, the liquid is retained by/between the plurality of the tooth cleaning elements 622, and the liquid oscillates in synchronization with the oscillation of the brush unit 620. Thus, the plaque removal effect can be heightened by removing the plaque adhered to the teeth with the oscillating liquid and the oscillating brush unit 620.

There are several different liquids that may be sprayed onto the teeth to provide a benefit when used with the electric toothbrush 600. In particular, as for the liquid put into the tank 630, when using a liquid having an effect of breaking up plaque, having this liquid be retained in the gaps between the tooth and the plurality of tooth cleaning elements 622, the breakup of plaque adhered to the tooth can be hastened, and the plaque removal effect is heightened. Also, as for the liquid put into the tank 630, when using a liquid having an effect of adhering to plaque and strengthening R light reflection, the plaque detection accuracy in the following plaque detection process can be heightened. Thus, two non-limiting examples for the liquid in the tank 630 includes a liquid with plaque breakup characteristics and a liquid with plaque adhering and R light reflection strengthening characteristics may be used. Of course, other liquids including those described throughout this document may also be used.

Note that the controller 650 may perform only the first drive or perform only the second drive while fluid is not being sprayed from the hole 621. For example, it could be made to be able to detect brushing pressure, and the controller 650 could perform the second drive when the brush pressure is high and perform the first drive when the brush pressure is low. Thus, there are many variations available and the controller 650 need not only alternate between the first and second drives, but rather may provide the best drive for a given circumstance. Also, in some embodiments the controller 650 could be made to detect the orientation of the electric toothbrush 600, so that the controller 650 may select whether to perform only the first drive, perform only the second drive, or perform a combination of the first drive and the second drive according to the detected orientation.

In certain embodiments, the controller 650 may identify the type of liquid stored in the tank 630, and perform the processes shown in FIG. 13 only when the type of liquid identified is a liquid other than water, and when the type of liquid identified is water, to perform a process that does not particularly limit the selection of the drive method in step S5 of FIG. 13.

For example, a button corresponding to the type of liquid may be provided on the gripping portion 610. The controller 650 identifies the type of liquid by which button is pressed. Alternatively, the tank 630 can be made a removable and attachable cartridge, and a tag with identification information is provided on the cartridge. Then, the controller 650 identifies the type of liquid by reading the identification information from the tag on the cartridge installed on the gripping portion 610. In this case, the controller 650 functions as a liquid identifying part. Many other techniques are possible to enable the controller 650 to determine what substance is contained within the tank 630 so that the controller 650 may alter its function based on the particular substance contained in the tank 630.

When the liquid sprayed from the hole 621 is water, plaque removal effect is obtained by having the water retained between the plurality of tooth cleaning elements 622. However, the plaque removal effect is bigger when the liquid sprayed from the hole 621 is a liquid other than water (an oral cleansing liquid or the like having a plaque breakup effect). Also, it is thought that when the liquid sprayed from the hole 621 is water, the plaque removal effect may be larger if the water is applied to the teeth with some force, more than retaining it between the plurality of tooth cleaning elements 622.

From these circumstances, it is best for the controller 650 to perform control that retains the liquid between the plurality of tooth cleaning elements 622 as in FIG. 13 to maximize the plaque removal effect, if the liquid in the tank 630 is a liquid other than water. Also, when the liquid is water, it is good for the controller 650 to perform only the first drive for oscillating the brush unit 620 in the first direction and to stop the second drive when liquid is being sprayed so that the water is not retained between the plurality of tooth cleaning elements 622 but is applied to teeth with some force in order to maximize the plaque removal effect when the liquid in the tank 630 is water. This configuration allows the optimum plaque removal effect to be obtained according to the liquid sprayed from the hole 621.

On the electric toothbrush 600, the light element 624 may be provided on the outer circumferential surface of the housing of the brush unit 620 (the same surface on which the tooth cleaning elements 622 extend). In this case, the light emitting element 624 functions as a light emission part. Also, the light receiving element 625 may be provided on the outer circumferential surface of the housing of the brush unit 620. According to the configuration of FIG. 10, the brush unit 620, which is a consumable (i.e., replaceable and discardable) good, needs only the transparent window 623 and the hole 621 added thereto relating to the ready-made product, and manufacturing cost can be significantly reduced. Thus, it may be preferable to keep all of the electronic components as a part of the stem 611 or some other component that is not the brush unit 620.

The second direction described above is preferably a direction perpendicular to the first direction. This makes the liquid sprayed from the hole 621 more easily retained between the plurality of tooth cleaning elements 622, and further heightens the plaque removal effect.

Certain components are described herein as forming a module. The module is generally a collection of components that form a unit that is intended to perform a particular function. Although the description provides specific examples of components that form each module, the invention is not to be so limited in all embodiments and less than all of the listed components may form the particular module being discussed. For example, in the description above the light emitting element 24, the transparent window 23a and the transparent window 23 may are described as collectively forming a light emitting module for emitting light from the brush unit 20. However, the light emitting module may comprise only the light emitting element 24 but not also the transparent windows 23, 23a in some embodiments. Thus, it should be appreciated that although the module is configured to perform a particular function, the invention should not be specifically limited by the exemplary embodiments described herein.

A program for executing each process carried out by the controller 50, 650 of the present embodiment may be provided in a computer. Such a program is recorded in a non-transitory recording medium readable by a computer.

Such a "computer readable recording medium" includes, for example, an optical medium such as a compact disc-ROM (CD-ROM) or a magnetic recording medium such as a memory card. In addition, such program may be provided by downloading via a network.

The embodiments disclosed herein are in all respects examples and are in no way considered to be limited thereto. The scope of the present invention is indicated by the scope of the patent claims and not by the descriptions given above and is intended to include all alternatives within equivalent meaning and scope to the patent claims.

As described above, the following matters are disclosed in the present specification.

The disclosed electric toothbrush includes: a driving unit for driving a brush unit mounted on the main body; a light emitting module for emitting light from the brush unit; a reflected light detecting module for detecting reflected light of the light emitted from the light emitting module; a stain sensing module for sensing a stain amount of a tooth based on the reflected light detected by the reflected light detecting module; a fluid spraying module for spraying fluid from the brush unit; and a fluid spray control unit for controlling the spray timing of the fluid based on the amount of reflected light detected by the reflected light detecting module.

In the disclosed electric toothbrush, the light emitting module emits a blue light, the reflected light detecting module detects individually a red light and a green light as the reflected light, the stain sensing module senses the stain amount of a tooth based on the red light, the fluid spray control unit sprays the fluid, in a first case in which the amount of red reflected light continues at not more than a first threshold and not less than a second threshold.

In the disclosed electric toothbrush, the fluid spray control unit, furthermore, sprays a fluid in a second case in a state in which the amount of red reflected light continues at not more than a third threshold and not less than a fourth threshold of time.

In the disclosed electric toothbrush, the fluid spray control unit, when the amount of red reflected light exceeds the third threshold, sprays a fluid in spray conditions differing from the spray conditions of the fluid in each of the first case and the second case.

In the disclosed electric toothbrush, the light emitting module emits a blue light, the reflected light detecting module detects a red light as the reflected light, the stain sensing module senses the stain amount of a tooth based on the red light, and the fluid spray control unit sprays the fluid, in a third case in which the amount of red reflected light continues at not more than a third threshold and not less than a fourth threshold of time.

In the disclosed electric toothbrush, the fluid spray control unit, when the amount of red reflected light exceeds the third threshold, sprays a fluid in spray conditions differing from the spray conditions of the fluid in the third case.

The method for operating the disclosed electric toothbrush is a method for operating an electric toothbrush having a drive module for driving a brush unit mounted on the main body, including: a light emitting step for emitting light from the brush unit; a reflected light detecting step for detecting reflected light of the emitted light; a stain sensing step for sensing a stain amount of a tooth based on reflected light detected by the reflected light detecting step; a fluid spray step for spraying fluid from the brush unit; and a fluid spray control step for controlling the spray timing of the fluid based on the amount of reflected light detected by the reflected light detecting step.

The disclosed electric toothbrush is provided with a driving portion that performs a first driving that oscillates a brush unit installed on a main body portion in a first direction that is the pressing direction of a plurality of brushes provided on the brush unit and a second driving that oscillates the brush unit in a second direction that is different from the first direction, and a fluid spraying unit that sprays a fluid from the brush unit, and the driving portion performs the first driving while the fluid is sprayed from the fluid spraying unit.

The disclosed electric toothbrush is further provided with a light emitting module that emits light from the brush unit, a reflected light detection portion that detects reflected light of the light emitted by the light emitting module, a stain sensing portion that senses tooth stain amount based on the reflected light detected by the reflected light detection portion, and a fluid spraying control unit that controls the spray timing of the fluid based on the light amount of the reflected light detected by the reflected light detection portion.

The disclosed electric toothbrush, wherein the light emitting module emits blue light, the reflected light detection portion individually detects red light and green light as reflected light, the stain sensing portion senses tooth stain amount based on the red light, and the fluid spraying control unit sprays the fluid in the first case where the state where the light amount of green reflected light at the first threshold or below continues at the second threshold or above.

The disclosed electric toothbrush, wherein the fluid spraying control unit further sprays the fluid in the second case where the state where the light amount of red reflected light at the third threshold or below continues at the second threshold or above.

The disclosed electric toothbrush, wherein the fluid spraying control unit sprays the fluid at spraying conditions different from the spraying conditions of the fluid in the first and second case respectively, in the case where the light amount of reflected red light exceeds the third threshold.

The disclosed electric toothbrush, wherein the light emitting module emits blue light, the reflected light detection portion detects red light as reflected light, the stain sensing portion senses tooth stain amount based on the red light, and the fluid spraying control unit sprays the fluid in the third case where the state where the light amount of red reflected light at the third threshold or below continues for a time at the fourth threshold or above.

The disclosed electric toothbrush, wherein the fluid spraying control unit sprays the fluid at spraying conditions different from the spraying conditions in the third case, in the case where the light amount of reflected red light exceeds the third threshold.

The disclosed electric toothbrush operation method is the electric toothbrush operation method provided with a driving step that performs the first driving that oscillates the brush unit installed on the main body portion of the electric toothbrush in the first direction which is the pressing direction of the plurality of brushes provided on the brush unit and the second driving that oscillates the brush unit in the second direction that is different from the first direction, and a fluid spraying step that sprays the fluid from the brush unit, and the first driving is performed while the fluid sprays in the fluid spraying step in the driving step.

The disclosed electric toothbrush is composed of a drive module for selectively performing a first drive for oscillating a brush unit installed on a main body in a first direction, which is the direction of pressing a plurality of brushes provided on the brush unit and a second drive for oscillating the brush unit in a second direction, which is different from the first direction; a light emitting module for emitting light from the brush unit; a reflected light detector for detecting reflected light of the light emitted from the light emitting module; a plaque detector for detecting plaque based on the reflected light detected by the reflected light detector; a liquid spray part for spraying liquid from a portion surrounded by the plurality of brushes from the brush unit; and a liquid spray controller for controlling the spray timing of the liquid; wherein the liquid spray controller sprays the liquid when the amount of plaque detected by the plaque detector exceeds a threshold, and the drive module stops the first drive and performs only the second drive while the liquid is being sprayed.

The disclosed electric toothbrush is further composed of a tank for storing the liquid and a liquid identification part for identifying the type of liquid stored in the tank, wherein the drive module implements a treatment such that the first drive is stopped and only the second drive is performed, only when the liquid identified by the liquid identification part is something other than water when the liquid is being sprayed.

The disclosed electric toothbrush includes things wherein the second direction is the direction perpendicular to the first direction.

The disclosed operating method of the electric toothbrush composed of a light emitting module for emitting light from a brush unit installed on the electric toothbrush, a reflected light detector for detecting the reflected light of the light emitted from the light emitting module, and a liquid spray part for spraying liquid from a portion surrounded by the plurality of brushes from the brush unit, is composed of a drive step for selectively performing a first drive for oscillating a brush unit installed on a main body in a first direction, which is the direction of pressing a plurality of brushes provided on the brush unit and a second drive for oscillating the brush unit in a second direction, which is different from the first direction, a plaque detection step for detecting plaque based on the reflected light detected by the reflected light detector, a liquid spray control step for spraying the liquid when the amount of plaque detected by the plaque detector exceeds a threshold, and within the drive step, the first drive is stopped and only the second drive is performed while the liquid is being sprayed.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An electric toothbrush comprising:
   a driving portion that performs a first driving that oscillates a brush unit in a first direction that is a pressing direction of a plurality of tooth cleaning elements provided on the brush unit and a second driving that oscillates the brush unit in a second direction that is different from the first direction;
   a fluid spraying unit that sprays a fluid from the brush unit;
   a light emitting module that emits light;
   a reflected light detection portion that detects reflected light of the light emitted by the light emitting module; and
   a controller configured to both activate the fluid spraying unit to spray the fluid and drive the driving portion to perform the first driving upon an amount of the reflected light detected by the reflected light detection portion being less than a first threshold.

2. The electric toothbrush according to claim 1 wherein the fluid sprayed from the fluid spraying unit is water.

3. An electric toothbrush comprising:
   a driving portion that performs a first driving that oscillates a brush unit in a first direction that is a pressing direction of a plurality of tooth cleaning elements provided on the brush unit and a second driving that oscillates the brush unit in a second direction that is different from the first direction;

a fluid spraying unit that sprays a fluid from the brush unit;

wherein the driving portion carries out the first driving while the fluid is being sprayed from the fluid spraying unit;

a light emitting module that emits light from the brush unit, the light emitting module emits blue light;

a reflected light detection portion that detects reflected light of the light emitted by the light emitting module, the reflected light detection portion detects the reflected light as red light and green light;

a stain sensing portion that senses tooth stain amount based on the reflected light detected by the reflected light detection portion, the stain sensing portion senses the tooth stain amount based on the red light; and a fluid spraying control unit that controls spray timing of the fluid based on an amount of the reflected light detected by the reflected light detection portion, the fluid spraying control unit sprays the fluid under a first condition when an amount of the green light detected by the reflected light detection portion is less than or equal to a first threshold for a period of time that is greater than or equal to a second threshold.

4. The electric toothbrush according to claim 3, wherein the fluid spraying control unit sprays the fluid under a second condition when an amount of the red light detected by the reflected light detection portion is less than or equal to a third threshold for a period of time that is greater than or equal to a fourth threshold.

5. The electric toothbrush according to claim 4, wherein the fluid spraying control unit sprays the fluid under a third condition that is different from the first and second conditions when the amount of the red light detected by the reflected light detection portion exceeds the third threshold.

6. The electric toothbrush according to claim 3, wherein the fluid spraying control unit sprays the fluid under a second condition when the amount of the red light detected by the reflected light detection portion is less than or equal to a third threshold for a period of time that is greater than or equal to a fourth threshold.

7. The electric toothbrush according to claim 6, wherein the fluid spraying control unit sprays the fluid under a third condition that is different from the second condition when the amount of the red light detected by the reflected light detection portion exceeds the third threshold.

8. An electric toothbrush comprising:
a body comprising a gripping part and a stem extending from the gripping part;
a brush unit detachably coupled to the body and having a plurality of tooth cleaning elements extending therefrom;
a drive assembly located in the body and configured to oscillate the brush unit, wherein the drive assembly is operably coupled to a controller to alternate operation of the drive assembly between at least: (1) a first mode wherein the drive assembly oscillates the brush unit in a first direction; and (2) a second mode wherein the drive assembly oscillates the brush unit in a second direction that is different than the first direction;
a fluid dispensing system for dispensing a fluid, the fluid dispensing system operably coupled to the controller to control operation of the fluid dispensing system; and
wherein when the fluid is being dispensed by the fluid dispensing system, the drive assembly only operates in the first mode.

9. The electric toothbrush according to claim 8 wherein the first direction is a pressing direction of the plurality of tooth cleaning elements provided on the brush unit.

10. The electric toothbrush according to claim 8 wherein the brush unit comprises a front surface, the plurality of tooth cleaning elements extending from the front surface, and wherein the first direction is perpendicular to the front surface of the brush unit in the direction that the plurality of tooth cleaning elements extend.

11. The electric toothbrush according to claim 8 wherein the second direction is perpendicular to the first direction.

12. The electric toothbrush according to claim 8 wherein the second direction is at least one of: (1) back-and-forth between distal and proximal ends of the brush unit; and (2) back-and-forth between opposing lateral sides of the brush unit.

13. The electric toothbrush according to claim 8 further comprising:
a light emitting element operably coupled to the controller and configured to emit light from the brush unit;
a light receiving element operably coupled to the controller and configured to receive reflected light of the light emitted from the light emitting element; and
wherein the controller controls operation of the fluid dispensing system based on an amount of the reflected light detected by the light receiving element.

14. The electric toothbrush according to claim 13 wherein the light emitting element emits blue light towards a tooth, and wherein the reflected light comprises a green light component corresponding to portions of the blue light that reflect off of exposed portions of the tooth and an red light component corresponding to portions of the blue light that reflect off of plaque on the tooth, and wherein the light receiving element transmits data to the controller indicative of an amount of the green light component and an amount of the red light component received by the light receiving element.

15. The electric toothbrush according to claim 14 wherein the controller is configured to operate the fluid dispensing system to dispense the fluid under a first condition when the amount of the green light component received by the light receiving element is less than or equal to a first threshold for a period of time that exceeds a second threshold.

16. The electric toothbrush according to claim 15 wherein the controller is configured to operate the fluid dispensing system to dispense the fluid under a second condition when the amount of the red light component received by the light receiving element is less than or equal to a third threshold for a period of time that exceeds a fourth threshold.

17. The electric toothbrush according to claim 16 wherein the controller is configured to operate the fluid dispensing system to dispense the fluid under a third condition when the amount of the red light component received by the light receiving element is greater than the third threshold.

18. The electric toothbrush according to claim 14 wherein the controller is configured to operate the fluid dispensing system to dispense the fluid under a first condition when the amount of the green light component received by the light receiving element is less than or equal to a first threshold for a period of time that exceeds a second threshold, wherein the controller is configured to operate the fluid dispensing system to dispense the fluid under a second condition when the amount of the red light component received by the light receiving element is less than or equal to a third threshold for a period of time that exceeds a fourth threshold, and wherein the controller is configured to operate the fluid dispensing system to dispense the fluid under a third condition when the amount of the red light component received by the light receiving element is greater than the third threshold.

19. The electric toothbrush according to claim 18 wherein the first and second conditions are the same and wherein the third condition is different than the first and second conditions, wherein the first and second conditions comprise dispensing a first amount of the fluid under a first pressure and wherein the third condition comprises dispensing a second amount of the fluid under a second pressure, at least one of the first and second amounts of fluid and the first and second pressures being different.

* * * * *